United States Patent
Cao

(10) Patent No.: US 11,931,361 B2
(45) Date of Patent: Mar. 19, 2024

(54) POXVIRUS HOST RANGE PROTEIN K3 AS A POSITIVE SELECTION MARKER FOR GENERATION OF RECOMBINANT POXVIRUSES, A THERAPEUTIC TARGET FOR POXVIRUS INFECTION AND A THERAPEUTIC AGENT FOR PKR RELATED DISEASES

(71) Applicant: Her Majesty the Queen in the Right of Canada as Represented by the Minister of Health, Winnipeg (CA)

(72) Inventor: Jingxin Cao, Winnipeg (CA)

(73) Assignee: Her Majesty the Queen in the Right of Canada as Represented by the Minister of Health, Winnipeg (CA)

( * ) Notice: Subject to any disclaimer, the term of this patent is extended or adjusted under 35 U.S.C. 154(b) by 796 days.

(21) Appl. No.: 17/049,439

(22) PCT Filed: Mar. 22, 2019

(86) PCT No.: PCT/CA2019/050355
§ 371 (c)(1),
(2) Date: Oct. 21, 2020

(87) PCT Pub. No.: WO2019/210392
PCT Pub. Date: Nov. 7, 2019

(65) Prior Publication Data
US 2021/0244739 A1    Aug. 12, 2021

Related U.S. Application Data

(60) Provisional application No. 62/666,356, filed on May 3, 2018.

(51) Int. Cl.
*A61K 31/519*    (2006.01)
*A61K 38/16*    (2006.01)
*C12N 7/00*    (2006.01)

(52) U.S. Cl.
CPC .......... *A61K 31/519* (2013.01); *A61K 38/162* (2013.01); *C12N 7/00* (2013.01); *C12N 2710/24021* (2013.01)

(58) Field of Classification Search
CPC ...... A61K 31/519; A61K 38/162; C12N 7/00; C12N 2710/24021
See application file for complete search history.

(56) References Cited

FOREIGN PATENT DOCUMENTS

WO    2007/092213    8/2007

OTHER PUBLICATIONS

McCausland, et al., Combination Therapy of Vaccinia Virus Infection with Human Anti-H3 and Anti-B5 Monoclonal Antibodies in a Small Animal Model, Antiviral Therapy, 15:661-675 (2010). (Year: 2010).*
Hand es, Haller SL, Peng C, Rothenburg S, Hersperger AR, "Ectopic expression of vaccinia virus E3 and K3 cannot rescue ectromrlia virus replication in rabbit RK13 cells". Plos One, Mar. 3, 2015, vol. 10, pp. e0119189.
Mudhasani R, Tran JP, Retterer C, Kota KP, Whitehouse CA, Bavaris, "Protein Kinase R Degradation Is Essential for Rift Valley Fever Virus Infection and Is Regulated by SKPI-CULI-F-box (SCF) FBXWII-NSs E3 Ligase". PLoS Pathog, Feb. 2, 2016, vol. 12, pp. e 1005437.
Zhang L, Villa NY, McFadden G, "Interplay between poxviruses and the cellular ubiquitin/ubiquitin-like pathways". FEBS Lett, Feb. 18, 2009, vol. 583, pp. 607-614.
Langland J O et al: "The Role of the PKR-Inhibitory Genes, E3L and K3L, in Determining Vaccinia Virus Host Range", Virology, vol. 299, No. 1, Jul. 20, 2002, pp. 133-141.
Park Chorong et al: "Species-Specific Inhibition of Antiviral Protein Kinase R by Capripoxviruses and Vaccinia virus: Species-Specific PKR Inhibition by Poxviruses", Annals or the New York Academy of Sciences, vol. 1438, No. 1. Feb. 1, 2019, pp. 18-29.
Le-Trilling Vu Thuy Khanh et al: "Broad and Potent Antiviral Activity of the NAE Inhibitor MLN4924", Scientific Reports, vol. 6, No. 1, Apr. 1, 2016.

* cited by examiner

*Primary Examiner* — Erich A Leeser
(74) *Attorney, Agent, or Firm* — Michael R Williams; Ryan W Dupuis; Ade & Company Inc.

(57) ABSTRACT

Described herein is a novel method for generation of recombinant poxviruses using an E3 and K3 double deletion mutant virus as the parental virus for generation of recombinant viruses. Following allowing for crossing over between the parental virus and an insertion cassette including an orthopox K3 peptide and the gene of interest, recombinant viruses are selected by infecting a host cell line permissive for the orthopox K3 peptide but not for the E3 and K3 double mutant parental virus. It is also demonstrated that a specific small molecule inhibitor of NEDD8 activating enzyme, MLN4924, can completely block poxvirus K3 family protein mediated PKR degradation and virus replication.

15 Claims, 16 Drawing Sheets
Specification includes a Sequence Listing.

|  | A | B | C |
|---|---|---|---|
| vvK3 | MLAFCYSLPNAGDVIKGFVYEKDYALYIYLFDYPHFEAILAESVKMHMDRYVEYRDKLVGKTVKVKVIRVDYTKGYIDVNYKRMCRHQ |
| TPox037 | MLAFCYSLPNVGDVLKGKVYENGYALYIILFDYPHSEAILAESVQMHMNRYFKYRDKLVGKTVKVKVIRVDYTKGYIDVNYKRMCRHQ |
| consensus | MLAFCYSLPNXGDVXKGXVYEXXYALYIXLFDYPHXEAILAESVXMHMXRYXXXYRDKLVGKTVKVKVIRVDYTKGYIDVNYKRMCRHQ | vvK3L/Tpox037 A
vvK3L/Tpox037 B
vvK3L/Tpox037 C

↓ Transfection and homologous recombination in HeLa/PKRko cells

VVΔE3L   K3L   ΔE3L

→ Select virus capable of replicating in HeLa cells

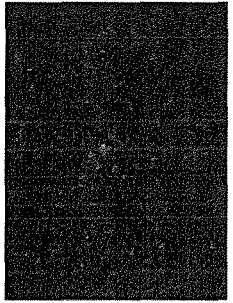  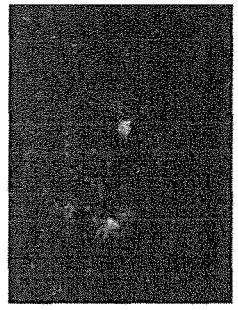 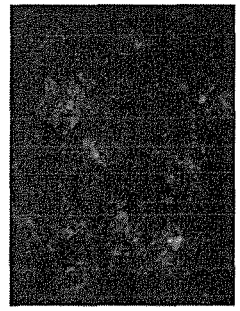
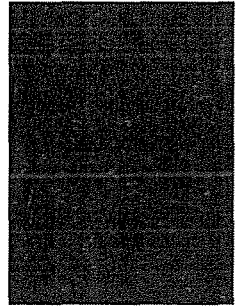 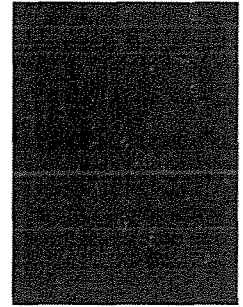 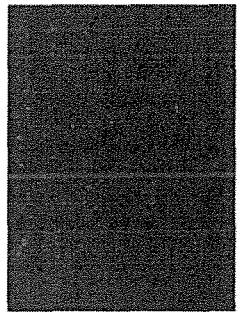 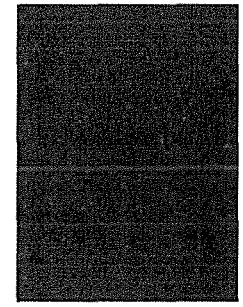
Figure 8B

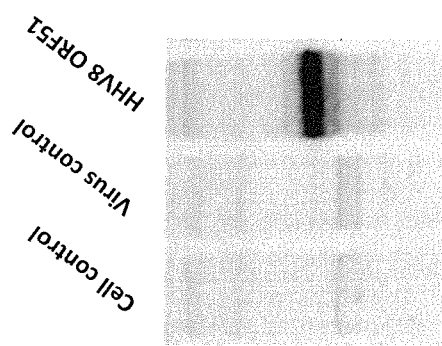
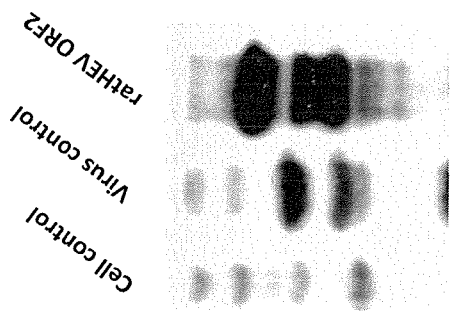
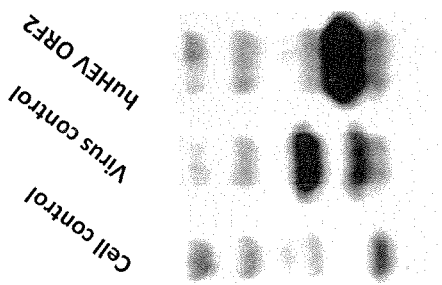
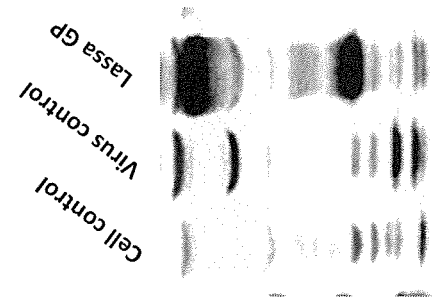
Figure 8C

Figure 9

```
Human eIF2αN    M--------PGL-SCRFYQHKFPEV-----EDVVMVNVRSIAEMGAYVSLLEYNNIEGMILLS-ELSRRRIRSIN-K
vvWR K3         M-----------------LAFCYSLPNA----GDVIKGRVYEKDYAL-YIYLFDYPHFEAILAESVKMHMDRYVEYRDK
Taterapox 037   M-----------------LAFCYSLPNV----GDVLKGKVYENGYAL-YIDLFDYPHSEAILAESVQMHMNRYFKYRDK
Sheeppox 011    M-----------------SSN-SDLAFCYVLPNI----NEVTDGIVCIRDNIV-YVKLINYG-LEALVIDYVNINMDQMNNIKKT
YMTV 012        M-----------------SRNRSQLAFCYAFPTV----GTITKGVTVEGDSF-TVFLPEFG-LHALIVNYLSVNVKRAKKLSEK
Swinepox 010    M-----------------STM-NTLAFCYGLPNI----NDITQGIIFVRNNIF-YSYLTDYA-MEACILNYINIRADKIEDLKKS
Myxoma 156      MTVIKPSSRPRPRKNKNIKVNTYRTSAMDLSPGSVHEGIVYFKDGIFKVRLLGYEGHECILLDYLNYRQDTLDR-LKER Human eIF2αN    LIRIGRNECVVVIRVDKEKGYIDLSKRRVSPEE        [94]
vvWR K3         L--VGKTVKVKVIRVDYTKGYIDVNYKRMCRHQ        [88]
Taterapox 037   L--VGKTVKVKVIRVDYTKGYIDVNYKRMCRHQ        [88]
Sheeppox 011    L--VNKLINVQIIRMNKIKGYIDVKIYNNN---        [89]
YMTV 012        L--SGKTVTVQVIRTDKLKGYVDVRHIE-----        [88]
Swinepox 010    L--VGKTISVRVIRVDVLKGYIDVSIV------        [86]
Myxoma 156      L--VGRVIKTRVVRAD--GLYVDLRRFF-----        [102]
```

Figure 11

| | OA3.Ts | HeLa | Vero E6 | PK15 |
|---|---|---|---|---|
| vvΔE3L/SPPV011wt | | | | |
| vvΔE3L/SPPV011/Y47H | | | | |

POXVIRUS HOST RANGE PROTEIN K3 AS A POSITIVE SELECTION MARKER FOR GENERATION OF RECOMBINANT POXVIRUSES, A THERAPEUTIC TARGET FOR POXVIRUS INFECTION AND A THERAPEUTIC AGENT FOR PKR RELATED DISEASES

PRIOR APPLICATION INFORMATION

The instant application is a 371 of PCT Application CA2019/050355, filed Mar. 22, 2019, which claims the benefit of US Provisional Application US Ser. No. 62/666, 356, filed May 3, 2018, now abandoned, and entitled "POXVIRUS HOST RANGE PROTEIN K3 AS A POSITIVE SELECTION MARKER FOR GENERATION OF RECOMBINANT POXVIRUSES", the entire contents of which are incorporated herein by reference for all purposes.

BACKGROUND OF THE INVENTION

Vaccinia virus, the prototypical member of the orthopoxvirus genus *Poxviridae*, is best known for its role in the immunization campaign to eradicate smallpox. While application of vaccinia virus as a vaccine for smallpox stopped in the 1980's due to the eradication of small pox, vaccinia virus has been developed for use as a recombinant vector for expressing foreign proteins for various purposes, e.g. recombinant vaccines or functional studies of a particular protein. The capability of vaccinia virus to express an unrelated foreign protein is largely due to its distinctive biological features: replicates exclusively in cytoplasm; large genome size with many "non-essential" loci for insertion of a foreign gene; and a broad range of host cells. (Moss, 1996 PNAS 93:11341).

Since the first description of the construction of a recombinant vaccinia virus (Panicali, Paoletti, PNAS, 79:4927; Mackett, et al., PNAS, 79:7415), many different methods of creating recombinant vaccinia virus have been developed. Although the in vitro ligation method of creating recombinant vaccinia virus can efficiently generate a library of recombinant vaccinia viruses expressing many different species of target proteins, the most widely used techniques to make recombinant vaccinia viruses are based on homologous recombination. Since the recombinant viruses produced during homologous recombination represent only a small percentage of the total virus population, a selection method is required to enrich and purify the desired recombinant viruses. The most commonly used techniques for selection of recombinant vaccinia viruses are: 1) positive selection with chemicals, for example, bromo-deoxyuridine for TK+ selection, or antibiotics, for example, gpt and neomycin resistance; and 2) colour marker based selection, such as β-gal and green fluorescence protein. While all of these methods work efficiently and are relatively simple to use for the selection of recombinant vaccinia virus, they are time-consuming and all require some form of non -poxvirus derived genes as selection markers, and this limits the applications of such recombinant viruses for human vaccines and/or therapeutics.

Described herein is a method of selecting recombinant poxviruses viruses using host range selection by poxvirus K3 proteins.

SUMMARY OF THE INVENTION

According to a first aspect of the invention, there is provided a method of preparing a recombinant poxvirus comprising:

providing a host cell comprising a parent poxvirus in which the coding sequences for native poxvirus E3 and K3 proteins have been disrupted or deleted, said host cell being permissive for growth of the parent poxvirus;

introducing an insertion cassette for inserting a gene of interest into the parent poxvirus genome at an insertion site into the host cell, said insertion cassette comprising a first crossover region, an expression cassette and a second crossover region, wherein the first crossover region has sufficient homology to an upstream region of the parent poxvirus genome that is upstream of the insertion site to initiate a crossover event with the parent poxvirus genome; the second crossover region has sufficient homology to a downstream region of the parent poxvirus genome that is downstream of the insertion site to initiate a crossover event with the parent poxvirus genome; and the insertion cassette comprises a first poxvirus promoter operably linked to a K3 ortholog for expression of the K3 ortholog from the first poxvirus promoter and a second poxvirus promoter operably linked to a gene of interest for expression of the gene of interest from the second poxvirus promoter;

subjecting the host cell to conditions permitting crossover events to occur between the insertion cassette and the parent poxvirus genome, subjecting the host cell to conditions suitable for generating a population of poxvirus particles, said population comprising parent poxvirus virus particles and recombinant poxvirus particles;

introducing said population into a second cell line non-permissive for growth of the parent poxvirus but permissive for growth of the recombinant poxvirus;

subjecting the second cell line to conditions promoting production of recombinant virus particles; and recovering the recombinant virus particles.

According to an aspect of the invention, there is provided a method of treating a poxvirus infection comprising administering to an individual in need of such treatment an effective amount of a compound of formula (VIIIa):

(VIIIa)

or a pharmaceutically acceptable salt thereof, wherein:
stereochemical configurations depicted at asterisked positions indicate relative stereochemistry;
Q is $C(R^k)$;
$R^a$ is —OH;
$R^b$ is hydrogen, fluoro, or $C_{1-4}$ aliphatic;
$R^c$ is hydrogen, —OH, or —OCH$_3$;
$R^d$ is hydrogen;
$R^8$ is hydrogen or $C_{1-4}$ aliphatic;
$R^k$ is hydrogen;
each $R^p$ independently is fluoro; —OR$^{5x}$; —N(R$^{4x}$)(R$^{4y}$); —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), —CO$_2$R$^{5x}$, or —C(O)N(R$^{4x}$)(R$^{4y}$); or $C_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$);

each $R^{8p}$ independently is fluoro; —$OR^{5x}$, —$N(R^{4x})(R^{4y})$; —$CO_2R^{5x}$; —$C(O)N(R^{4x})(R^{4y})$; $C_{1-4}$ aliphatic optionally substituted with —$OR^{5x}$, —$N(R^{4x})(R^{4y})$, —$CO_2R^{5x}$, or —$C(O)N(R^{4x})(R^{4y})$; or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; provided that when two $R^{8p}$ are attached to the same carbon atom, one must be selected from the group consisting of fluoro; —$CO_2R^{5x}$; —$C(O)N(R^{4x})(R^{4y})$; $C_{1-4}$ aliphatic optionally substituted with —$OR^{5x}$, —$N(R^{4x})(R^{4y})$, $CO_2R^{5x}$, or —$C(O)N(R^{4x})(R^{4y})$; and $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; or two $R^{8p}$ on the same carbon atom together form ═O or ═$C(R^{5x})_2$;

$R^{4x}$ is hydrogen, $C_{1-4}$ alkyl, $C_{1-4}$ fluoroalkyl, or $C_{6-10}$ ar($C_{1-4}$ )alkyl, the aryl portion of which is optionally substituted;

$R^{4y}$ is hydrogen; $C_{1-4}$ alkyl; $C_{1-4}$ fluoroalkyl; $C_{6-10}$ ar($C_{1-4}$)alkyl, the aryl portion of which is optionally substituted; optionally substituted 5- or 6-membered aryl; optionally substituted heteroaryl; or optionally substituted heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from the group consisting of N, O, and S;

each $R^{5x}$ independently is hydrogen, $C_{1-4}$ alkyl, $C_{1-4}$ fluoroalkyl, or an optionally substituted $C_{6-10}$ aryl, or optionally substituted $C_{6-10}$ ar($C_{1-4}$ )alkyl;

wherein:

in each recitation of optionally substituted aryl, the aryl group, when substituted, contains on one or more unsaturated carbon atoms a substituent independently selected from the group consisting of halo, —$NO_2$, —CN, —R*, —C(R*)═C(R*)$_2$, —C≡C—R*, —OR*, —$SR^o$, —$S(O)R^o$, —$SO_2R^o$, —$SO_2N(R^+)_2$, —$N(R^+)_2$, —$NR^+C(O)R*$, —$NR^+C(O)N(R^+)_2$, —$NR^+CO_2R^o$, —O—$CO_2R*$, —$OC(O)N(R^+)_2$, —O—C(O)R*, —$CO_2R*$, —C(O)—C(O)R*, —C(O)R*, —$C(O)N(R^+)_2$, —$C(═NR^+)$—$N(R^+)_2$, —$C(═NR^+)$—OR*, —$N(R^+)$—$N(R^+)_2$, —$N(R^+)C(═NR^+)$—$N(R^+)_2$, —$NR^+SO_2R^o$, —$NR^+SO_2N(R^+)_2$, —$P(O)(R*)_2$, —$P(O)(OR*)_2$, —O—P(O)—OR*, and —$P(O)(NR^+)$—$N(R^+)_2$;

in each recitation of optionally substituted heteroaryl, the heteroaryl group, when substituted, if on an unsaturated carbon atom, contains on one or more unsaturated carbon atoms, a substituent independently selected from the group consisting of halo, —$NO_2$, —CN, —R*, —C(R*)═C(R*)$_2$, —C≡C—R*, —OR*, —$SR^o$, —$S(O)R^o$, —$SO_2R^o$, —$SO_2N(R^+)_2$, —$N(R^+)_2$, —$NR^+C(O)R*$, —$NR^+C(O)N(R^+)_2$, —$NR^+CO_2R^o$, —O—$CO_2R*$, —$OC(O)N(R^+)_2$, —O—C(O)R*, —$CO_2R*$, —C(O)—C(O)R*, —C(O)R*, —$C(O)N(R^+)_2$, —$C(═NR^+)$—$N(R^+)_2$, —$C(═NR^+)$—OR*, —$N(R^+)$—$N(R^+)_2$, —$N(R^+)C(═NR^+)$—$N(R^+)_2$, —$NR^+SO_2R^o$, —$NR^+SO_2N(R^+)_2$, —$P(O)(R*)_2$, —$P(O)(OR*)_2$, —O—P(O)—OR*, and —$P(O)(NR^+)$—$N(R^+)_2$, and, if on a substitutable nitrogen atom, contains on one or more substitutable nitrogen atoms, a substituent independently selected from the group consisting of —R*, —N(R*)$_2$, —C(O)R*, —$CO_2R*$, —C(O)—C(O)R*, —$C(O)CH_2C(O)R*$, —$SO_2R*$, —$SO_2N(R*)_2$, —C(═S)N(R*)$_2$, —C(═NH)—N(R*)$_2$, and —$NR*SO_2R*$; and in each recitation of optionally substituted heterocyclyl, the heterocyclyl group, when substituted, if on a saturated carbon atom, contains on one or more saturated carbon atoms, a substituent independently selected from the group consisting of halo, —$NO_2$, —CN, —R*, C(R*)═C(R*)$_2$, —C≡—C—R*, —OR*, —$SR^o$, —$S(O)R^o$, —$SO_2R^o$, —$SO_2N(R^+)_2$, —$N(R^+)_2$, —$NR^+C(O)R*$, —$NR^+C(O)N(R^+)_2$, —$NR^+CO_2R^o$, —O—$CO_2R*$, —$OC(O)N(R^+)_2$, —O—C(O)R*, —$CO_2R*$, —C(O)—C(O)R*, —C(O)R*, —$C(O)N(R^+)_2$, —$C(═NR^+)$—$N(R^+)_2$, —$C(═NR^+)$—OR*, —$N(R^+)$—$N(R^+)_2$, —$N(R^+)C(═NR^+)$—$N(R^+)_2$, —$NR^+SO_2R^o$, —$NR^+SO_2N(R^+)_2$, —$P(O)(R*)_2$, —$P(O)(OR*)_2$, —O—P(O)—OR*, and —$P(O)(NR^+)$—$N(R^+)_2$, ═O, ═S, ═C(R*)$_2$, ═N—$N(R^+)_2$, ═N—OR*, ═N—NHC(O)R*, ═N —$NHCO_2R^o$, ═N—$NHSO_2R^o$, and ═N—R*, and, if on a substitutable nitrogen atom, contains on one or more substitutable nitrogen atoms, a substituent independently selected from the group consisting of —R*, —N(R*)$_2$, —C(O)R*, —$CO_2R*$, —C(O) —C(O)R*, —$C(O)CH_2C(O)R*$, —$SO_2R*$, —$SO_2N(R*)_2$, —C(═S)N(R*)$_2$, —C(═NH) —N(R*)$_2$, and —$NR*SO_2R*$;

wherein:

each occurrence of $R^o$ is independently an aliphatic or aryl group;

each occurrence of $R^+$ is independently hydrogen or an aliphatic, aryl, heteroaryl, or heterocyclyl group, or two $R^+$ on the same nitrogen atom, taken together with the nitrogen atom, form a five to eight membered aromatic or non-aromatic ring having, in addition to the nitrogen atom, zero to two ring heteroatoms independently selected from the group consisting of N, O, and S; and each occurrence of R* is independently hydrogen, aliphatic, aryl, heteroaryl, or heterocyclyl group;

s is 0, 1, or 2; and t is 0, 1, or 2.

FIG. 3. Replication of VVΔE3LΔK3L/SPV010 and YMTV012 in sheep cell OA3.Ts cells. The plaque images were taken at 24, 48 and 72 hours post infection.

FIG. 4. Poxviurs K3 orthologs, SPPV011, TPox037 and YMTV012, mediate PKR degradation, which is blocked by the NEDD8 activating enzyme (NAE) inhibitor MLN4924. HeLa cells were infected with the indicated viruses at a multiplicity of infection (moi) of 10 with (4B) or without (4A) MLN4924. The cell lysate was collected at the times indicated. A PKR antibody which can bind to both the non-phosphorylated and phosphorylated PKR (but with higher affinity for the phosphorylated PKR) was used in the Western blotting. The MLN4924 concentration was used at 10 μM.

Figure 5:
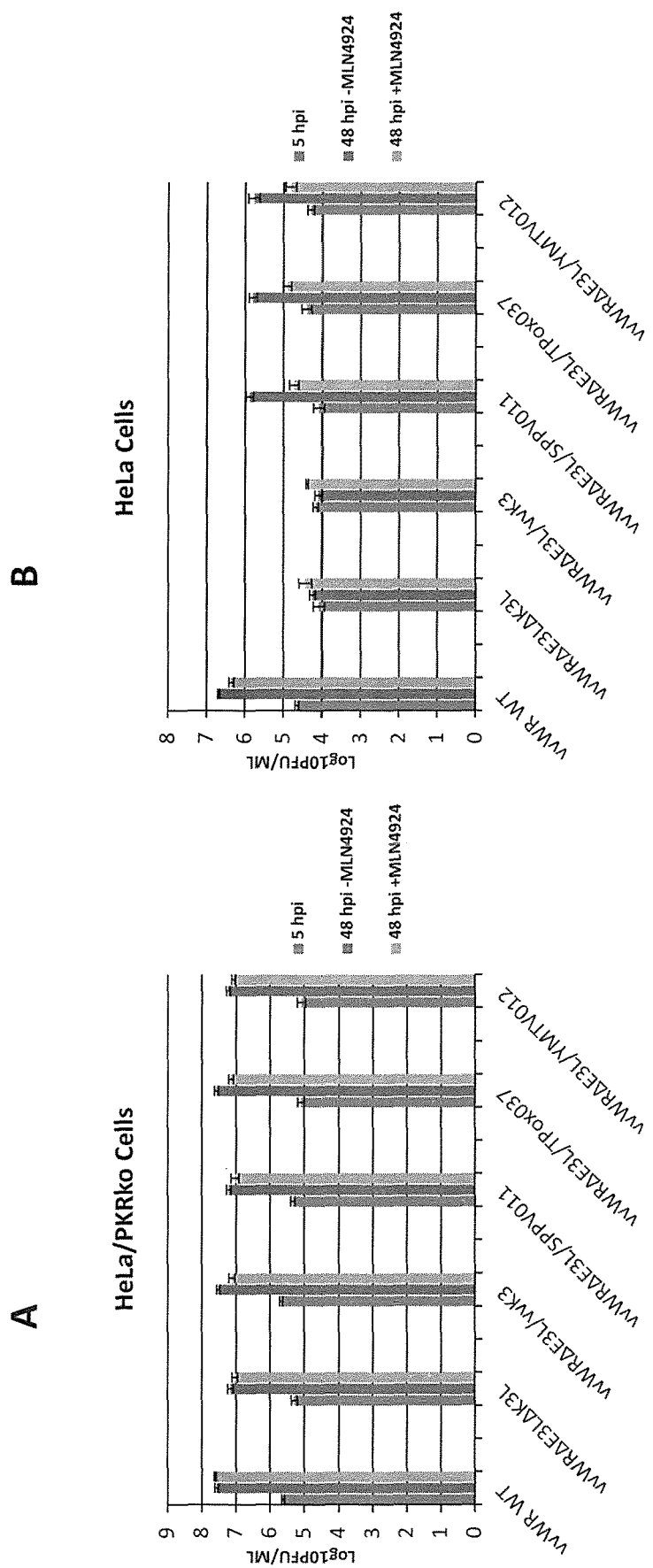

FIG. 5. The NAE inhibitor MLN4924 inhibits the poxvirus K3 ortholog restored virus replication in HeLa cells (5B), but not in HeLa/PKRko cells (5A). HeLa or HeLa/PKRko cells were infected with the indicated viruses at a multiplicity of infection (moi) of 10. After 1 hour of incubation, the cells were washed 3 times with PBS, fresh medium with or without 10 μM MLN4924 was added, and the virus was collected at 5 and 48 hours post infection. The virus replication was represented by the increase between the 5 and 48 hpi.

Figure 6:
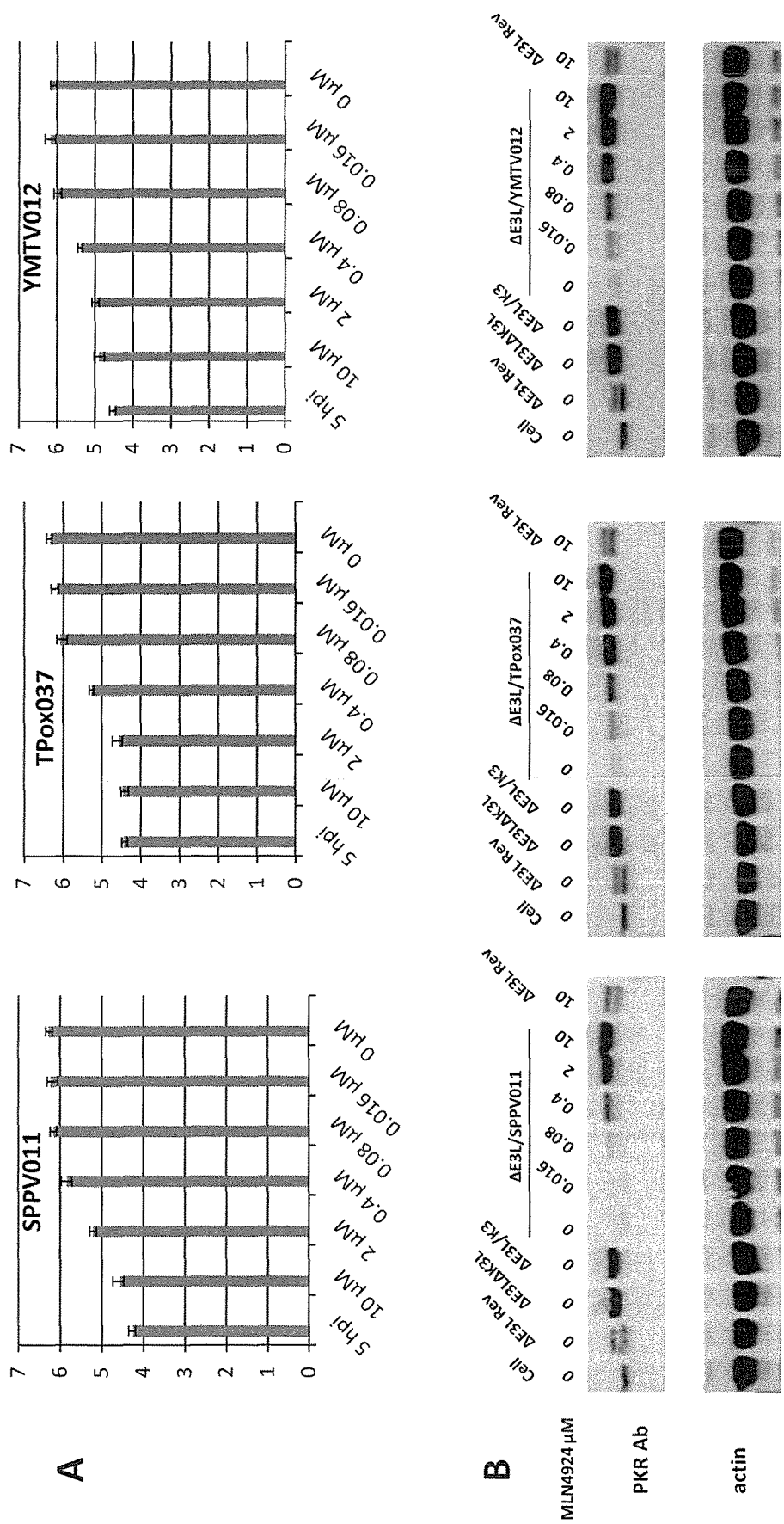

FIG. 6. The NAE inhibitor MLN4924 demonstrates dose-dependent inhibition of poxvirus K3 ortholog mediated virus replication and PKR degradation in HeLa cells. A: HeLa cells were infected as in FIG. 5, but with a series of 5-fold dilutions of MLN4924, ranging from 10 μM to 0.016 μM. B: HeLa cells were infected with an moi of 10 as in FIG. 4 and cell lysate was collected at 12 hpi and subject to Western blotting with the PKR antibody.

Figure 4:
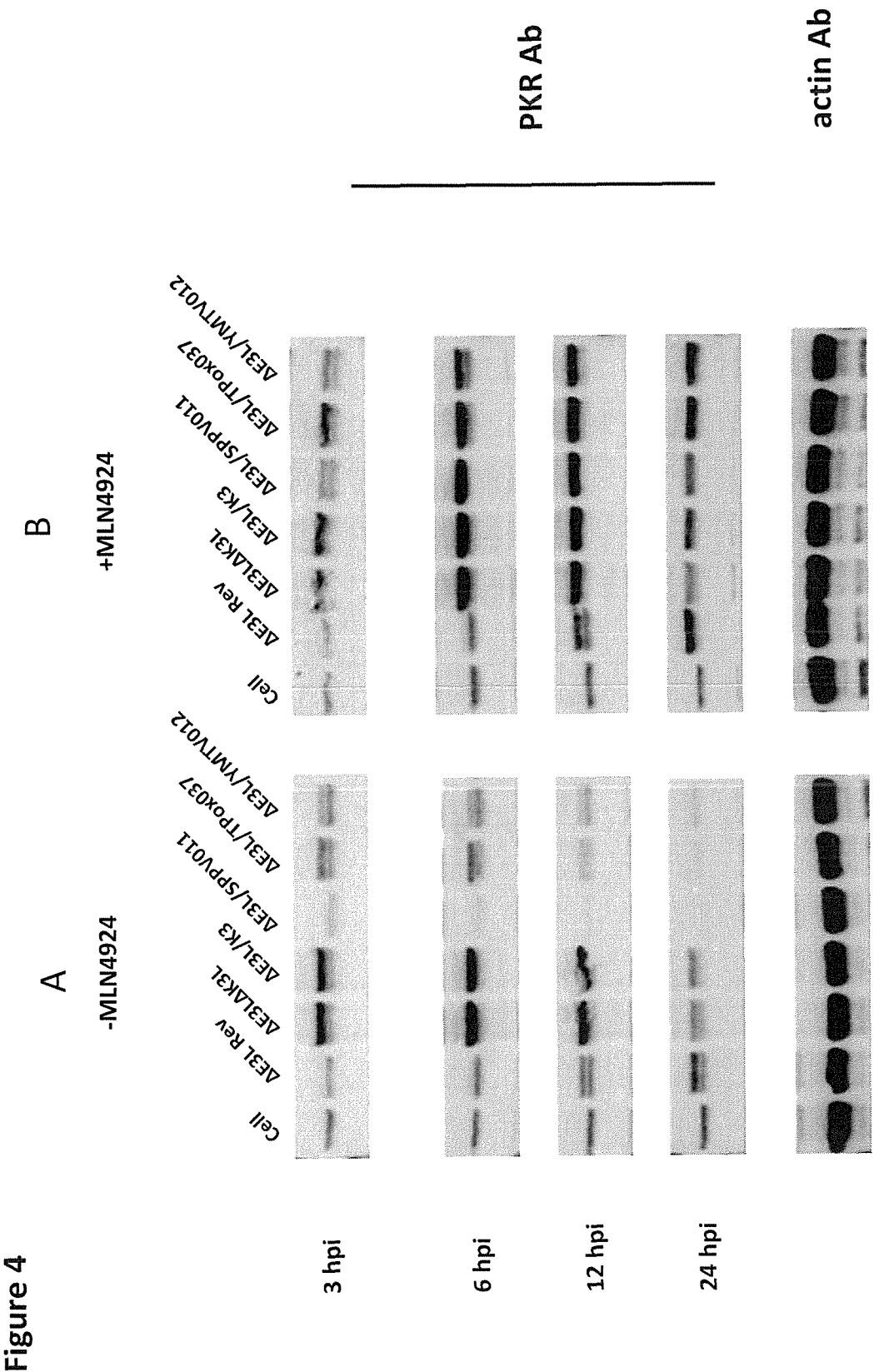

FIG. 7. Identification of the motif in the TPox037 critical for mediating virus replication and PKR degradation in HeLa cells. A: Alignment of vaccinia K3 (SEQ ID No: 2) and TPox037 (SEQ ID No: 3) form a consensus (SEQ ID No: 13) including domain C (SEQ ID No: 12) and are used for the design of chimeric constructs with vaccinia K3 backbone and TPox037 motifs. B: Replication of the chimeric K3 and TPox037C motif recombinant in HeLa cells with and without MLN4924. C: Degradation of PKR mediated by the chimeric K3TPOx037C. All of the infections were carried out as shown in FIGS. 4 and 5.

FIG. 8. Application of poxvirus K3 ortholog as a positive host range selection marker for generation of recombinant vaccinia virus. A: schematic illustration of the procedure to generate recombinant vaccinia virus expressing a foreign using TPox037 as a selection marker. B: replication of the recombinant virus at different passages, BHK21 cells were used and the image was taken at 24 hpi with 5× magnification. C: Expression of the protein of interest as detected by Western blotting with the FLAG tagged Ab. For, Lassa GP, human HEV ORF2 and rat HEV ORF2, HeLa cells were used; for HHV8 ORF51, Huh7 cells were used.

FIG. 9. Alignment of peptide sequences of Human eIF2αN (SEQ ID No: 1), vvWR K3 (SEQ ID No: 2), Taterapox 037 (SEQ ID No: 3), Sheeppox 011 (SEQ ID No: 4), YMTV 012 (SEQ ID No: 5), Swinepox 010 (SEQ ID No: 6) and Myoxma 156 (SEQ ID No: 7).

Figure 10:
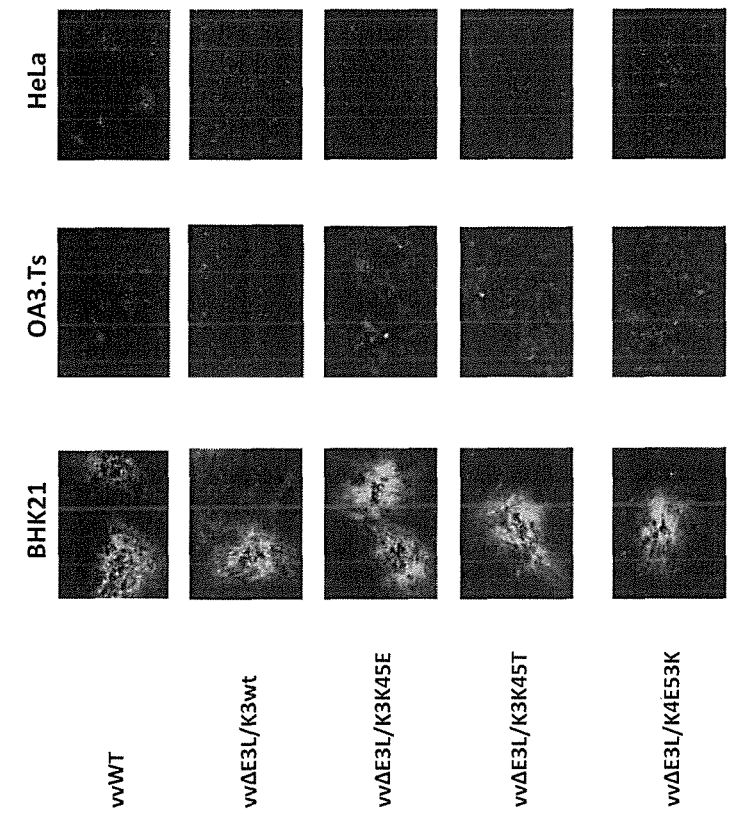

FIG. 10. Single point mutation in the K3 protein can restore vvΔE3L replication in OA3.Ts cells, but not in HeLa cells.

FIG. 11. Single point mutation Y47H in the sheeppoxvirus K3 ortholog SPPV011 rendered the virus unable to replicate in HeLa (human), Vero (monkey) and PK15 (pig) cells.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Most vertebrate poxviruses encode two Protein kinase RNA-activated or protein kinase R or interferon-induced, double-stranded RNA-activated protein kinase or eukaryotic translation initiation factor 2-alpha kinase (PKR) antagonists, E3 (a dsRNA binding protein) and K3 (an eIF2α homolog), which are important for the virus host range. Described herein is a method of selecting for recombinant viruses using host range selection by rescue of an essential gene to make a recombinant poxvirus.

The best known Vaccinia host range gene is the E3L, which encodes a protein inhibiting PKR mediated antiviral activities. In cell cultures, E3 protein tends to be the predominant suppressor of PKR, while the deletion of the K3L gene alone (with an intact E3L) often does not cause a defect in the virus resistance to PKR induced antiviral activity. Replication of the E3L deletion mutant vaccinia virus (VVΔE3L) is completely aborted in many cell lines, e.g HeLa cells and sheep cells OA3.Ts, while the deletion mutant virus still remains replication competent in certain cells, such as BHK21 cells.

As discussed herein, the invention takes advantage of the gain/loss of this host range phenotype as the basis to select recombinant vaccinia viruses.

The K3 protein encoded by vaccinia is a homolog of eukaryotic translation initiation factor 2α and was believed to be a pseudo-substrate for PKR. That is, the prior art teaches that K3 acts as a pseudo-substrate for PKR, thereby reducing PKR interaction with its proper cellular substrates. Thus, similar to the E3 protein, the K3 protein inhibits PKR mediated antiviral activity. However, vaccinia K3 protein cannot compensate for the loss of E3 protein in most of the cell lines tested to date, including many human cells, such as HeLa.

As discussed herein, in a comparative examination of poxvirus K3L orthologs, a vaccinia mutant virus with both E3L and K3L genes deleted (vvAE3LΔK3L) was used to express several poxvirus K3 othologs, including teterapox virus (an orthopoxvirus) 037 (TPox037), a sheeppox virus orthologs 011 (SPPV011), Yaba monkey tumor virus 012 (YMTV012), suipoxvirus 010 (SPV010) and myxomavirus 156 (M156).

Figures 1, 2:
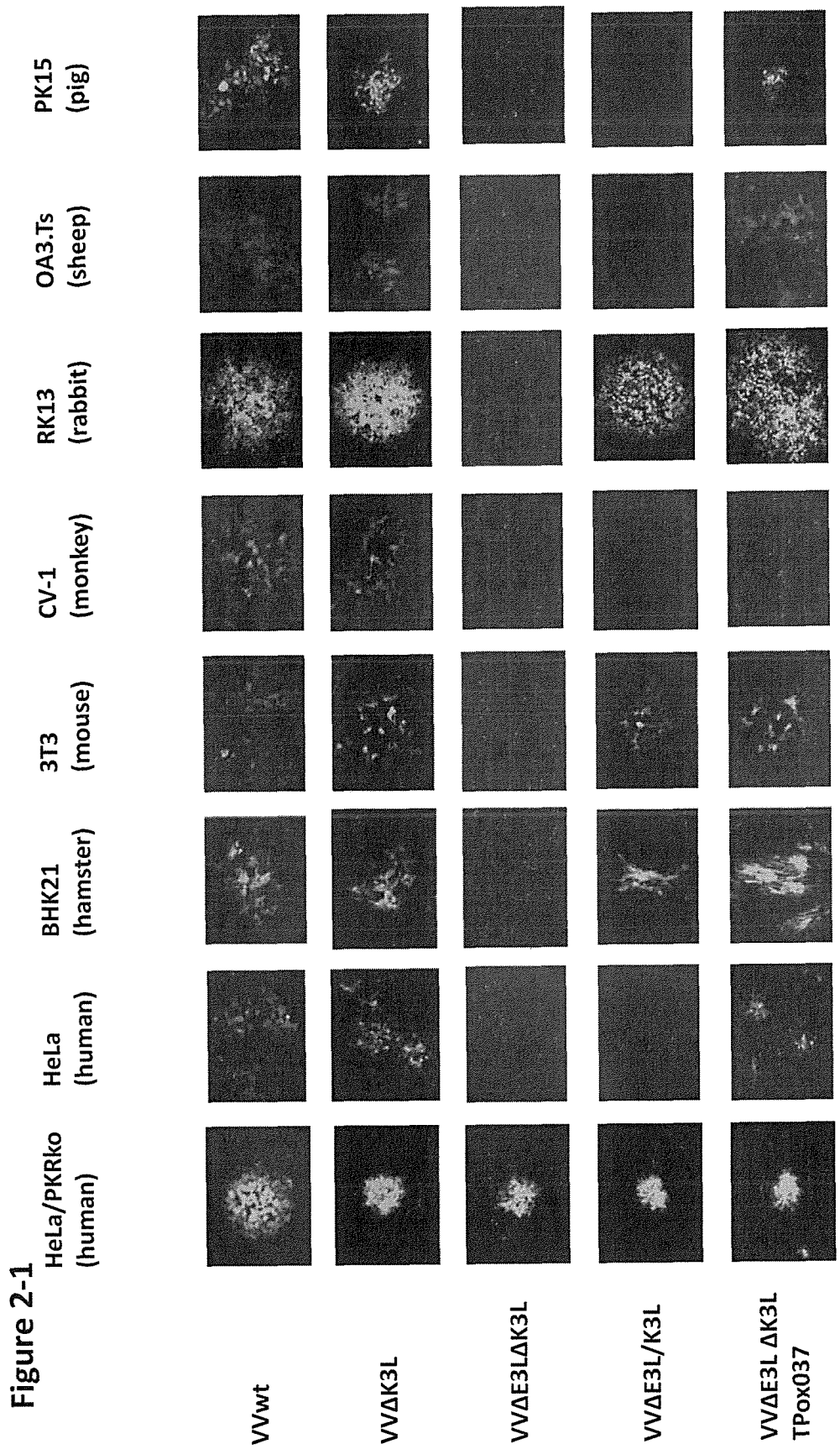
FIG. 2. Replication of the VVΔE3LΔK3L expressing poxvirus K3 orthologs and the control viruses in a variety of cell lines derived from different host species. The cell monolayer was infected with corresponding viruses and the images of virus plaques were taken at 24 hours post infection with 10× magnification.

It was found that the K3 orthologs of those highly species-restrictive poxviruses (sheeppox, myxoma, YMTV and suipoxvirus) could all restore the vvΔE3LΔK3L to replicate in their corresponding host cells, although some showed broader host range than others, as shown in FIG. 2 and summarized in Table 1.

Interestingly, TPox037, SPPV011 and YMTV012 are able to restore the replication of vvΔE3LΔK3L in human cells, such as HeLa, a cell line that vaccinia K3 cannot replicate in, as discussed herein.

As discussed below, further investigation revealed that these poxvirus K3 ortholog proteins restored the virus replication through mediating degradation of cellular protein kinase R (PKR) in a neddylation of cullin-ring ligase dependent manner.

Furthermore, as discussed below, a specific small molecule inhibitor of NEDD8 activating enzyme, MLN4924, can completely block poxvirus K3 family protein mediated PKR degradation and virus replication. Accordingly, the small molecule MLN4924 can be used as a therapeutic agent to treat a poxvirus infection, as discussed herein.

Described herein is a novel selection method based on this newly discovered property of poxvirus K3 orthologs by using the vaccinia E3L and K3L double deletion mutant virus (vvΔE3LΔK3L) as the parental virus for generation of recombinant vaccinia virus. This novel strategy for construction of a recombinant vaccinia virus is highly valuable for the development of vaccines, therapeutic agents and other applications related to recombinant poxviruses, as discussed herein.

According to an aspect of the invention, there is provided a method of preparing a recombinant poxvirus comprising:

providing a host cell comprising a parent poxvirus in which the coding sequences for native poxvirus E3 and K3 proteins have been disrupted or deleted, said host cell being permissive for growth of the parent poxvirus;

introducing an insertion cassette for inserting a gene of interest into the parent poxvirus genome at an insertion site into the host cell, said insertion cassette comprising a first crossover region, an expression cassette and a second crossover region, wherein the first crossover region has sufficient homology to an upstream region of the parent poxvirus genome that is upstream of the insertion site to initiate a crossover event with the parent poxvirus genome; the second crossover region has sufficient homology to a downstream region of the parent poxvirus genome that is downstream of the insertion site to initiate a crossover event with the parent poxvirus genome; and the insertion cassette comprises a first poxvirus promoter operably linked to a K3 ortholog for expression of the K3 ortholog from the first poxvirus promoter and a second poxvirus promoter operably linked to a gene of interest for expression of the gene of interest from the second poxvirus promoter;

subjecting the host cell to conditions permitting crossover events to occur between the insertion cassette and the parent poxvirus genome, subjecting the host cell to conditions suitable for generating a population of poxvirus particles, said population comprising parent poxvirus virus particles and recombinant poxvirus particles; and introducing said population into a second cell line non-permissive for growth of the parent poxvirus but permissive for growth of the recombinant poxvirus;

subjecting the second cell line to conditions promoting production of recombinant virus particles; and recovering the recombinant virus particles.

As will be appreciated by one of skill in the art, "deleted" indicates that a significant portion, for example, substantially all of the coding sequence has been removed whereas "disrupted" indicates that the intact coding sequence has been interrupted, for example, by insertion into the coding sequence or removal of part of the coding sequence so that a functional gene product is not produced.

According to another aspect of the invention, there is provided a method of preparing a recombinant poxvirus comprising:

providing a host cell comprising a parent poxvirus in which the coding sequences for native poxvirus E3 and K3 proteins have been disrupted or deleted, said host cell being permissive for growth of the parent poxvirus;

introducing an insertion cassette for inserting a gene of interest into the parent poxvirus genome at an insertion site into the host cell, said insertion cassette comprising a first crossover region, an expression cassette and a second crossover region, wherein the first crossover region has sufficient homology to an upstream region of the parent poxvirus genome that is upstream of the insertion site to initiate a crossover event with the parent poxvirus genome; the second crossover region has sufficient homology to a downstream region of the parent poxvirus genome that is downstream of the insertion site to initiate a crossover event with the parent poxvirus genome; and the insertion cassette comprises a first poxvirus promoter operably linked to a K3 ortholog for expression of the K3 ortholog from the first poxvirus promoter and a second poxvirus promoter operably linked to a gene of interest for expression of the gene of interest from the second poxvirus promoter;

crossover events occurring between the insertion cassette and the parent poxvirus genome, thereby generating a population of poxvirus particles, said population comprising parent poxvirus virus particles and recombinant poxvirus particles; and introducing said population into a second cell line non-permissive for growth of the parent poxvirus but permissive for growth of the recombinant poxvirus;

producing recombinant virus particles in the second cell line; and recovering the recombinant virus particles.

In some embodiments, the expression cassette is between the first crossover region and the second crossover region. That is, the expression cassette is flanked by the first crossover region and the second crossover region. That is, the insertion cassette comprises, in order or in sequence, the first crossover region, the expression cassette and the second crossover region. As will be apparent to one of skill in the art, the insertion cassette is a nucleic acid molecule comprising in order or in sequence the first crossover region, the expression cassette and the second crossover region. It is of note that the insertion cassette may be a circular nucleic acid molecule or a linear nucleic acid molecule.

As will be apparent to one of skill in the art, the insertion site within the parent poxvirus may be any location within the poxvirus genome that will tolerate an insertion, that is, that will not disrupt an important locus, for example, a coding region or a regulatory region.

In some embodiments, the insertion site is within or proximal to the deleted or disrupted K3 gene. In these embodiments, the first crossover region corresponds to a region of K3L FL (K3L left flanking region) and the second crossover region corresponds to K3L RL (K3L right flanking region).

In other embodiments, the first crossover region and the second crossover region respectively are nucleic acid molecules that are substantially identical to the nucleic acid sequences flanking the insertion site. As will be appreciated by one of skill in the art, in order to have sufficient homology to initiate or terminate the crossover event, the first crossover region and the second crossover region may be at least 50 base pairs long, at least 75 base pairs long, at least 100 base pairs long, at least 125 base pairs long, at least 150 base pairs long, at least 175 base pairs long, at least 200 base pairs long, at least 225 base pairs long, at least 250 base pairs long, at least 275 base pairs long or at least 300 base pairs long and may have at 95% identity, at least 96% identity, at least 97% identity, at least 98% identity or at least 99% identity or about 100% identity to the poxvirus genome sequence.

As will be known to those of skill in the art, poxvirus crossover events of this nature can generally tolerate a distance of up to 25 kb between crossover regions or flanking regions or homologous recombination regions. As such, in some embodiments, the first crossover region and the second crossover region are 25 Kb or less apart in the insertion cassette. As will be appreciated by one of skill in the art, the sections of the parent virus genome homologous to or corresponding to the first crossover region and the second crossover region may be separated by a shorter distance.

Accordingly, as will be appreciated by one of skill in the art, the expression cassette may comprise more than one, at least two, at least three, at least four or more than four genes of interest.

As will be appreciated by one of skill in the art, such a construct has several advantages, as for example antigens against several common diseases or diseases of concern could be administered using a single viral construct.

As will be appreciated by one of skill in the art, the terms "upstream" and "downstream" are largely relative terms and are intended to show the relative orientation of the respective elements.

As will be apparent to one of skill in the art, in some cases, only about 1% of the virus particle population will be recombinant viruses. However, because of the use of a host cell that is only permissive for the recombinant virus, only recombinant viruses can grow, thereby making recovery of the desired particles much simpler.

In some embodiments, the recombinant poxvirus and/or the parent poxvirus is a vaccinia virus.

In some embodiments, the expression cassette comprises an expression detector.

As will be appreciated by one of skill in the art and as discussed herein, the expression detector may be any suitable element that allows for detection of expression from the expression cassette and/or facilitates identification of cells comprising the expression cassette (inserted in the recombinant virus genome). Thus, this expression detector may be used as a means to facilitate the detection of cells comprising the recombinant virus; however, as will be appreciated by one of skill in the art, selection of cells expressing the recombinant virus for isolation of the virus particles may not be necessary for recovery of recombinant virus particles. Furthermore, virus-infected cells can be detected even without adding an expression detector.

As will be apparent to one of skill in the art, the recombinant viruses may be recovered from the cells of the second cell line, for example, the cells of the second cell line infected with the recombinant virus particles, using any suitable means known in the art for virus recovery.

In some embodiments, the K3 ortholog is selected from the group consisting of: teterapox virus (an orthopoxvirus) 037 (TPox037) (SEQ ID No: 3), a sheeppox virus orthologs 011 (SPPV011) (SEQ ID No: 4), Yaba monkey tumor virus 012 (YMTV012) (SEQ ID No: 5), suipoxvirus 010 (SPV010), myxomavirus 156 (M156) (SEQ ID No: &) and a synthetic or artificial K3 peptide for example SEQ ID Nos: 8, 9, 10 or 11 or a synthetic K3 peptide comprising a modified domain C (SEQ ID No: 12). As discussed herein, in these embodiments the K3 orhtolog gene from other poxvirsues such as taterapoxvirus, sheeppox virus and the like is synthesized and/or modified and inserted into vaccinia virus.

As shown in FIGS. 2, 9, 10 and 11 and in Table 1 and as discussed herein, different K3 orthologs permit replication in different cell types.

While not wishing to be bound to a particular theory or hypothesis, it is believed that each K3 ortholog has a specific domain that interacts with PKR for promoting neddylation-mediated degradation of PKR, likely in a species-specific manner, although as shown in Table 1 and FIG. 2, there are some orthologs which appear to be capable of interacting with PKR of other species. However, the simple binding between K3 and PKR is not sufficient to degrade the PKR protein, the PKR protein needs to be ubiquitinated by cellular cullin-ring ligase complex. As such, it is possible that K3 functions as a mediator or adaptor to link PKR to the cellular cullin-ring ligase complex. In this hypothesis, K3 does not bind to NEDD8 directly, but NEDD8 is an activator of cullin-ring ligase. MLN4924 prevents this NEDD8 activation of the cullin-ring ligase (which is the engine to ubiquitinate substrate proteins such as PKR).

As discussed below, the species-specificity of K3 has been localized to a small domain within K3. For example, this is clearly shown in FIG. 7, wherein it is demonstrated that exchanging of only 4 amino acids within an 11 amino acid domain of a K3 ortholog into a vaccinia K3 backbone is sufficient to permit viral replication in a cell line that is non-permissive for native the parental vaccinia virus (vvΔE3LΔK3L). That is, by swapping only 4 amino acids shown in the motif designated as TPox037C, we can change the function of vaccinia K3 protein from not mediating degradation of PKR in for example HeLa cells to mediating degradation of PKR in HeLa cells. However, as discussed below, swapping the other two regions of non-identity or motifs, designated as TPox037A and B, has no effect on K3 activity, that is, a K3 peptide recombined over motifs TPox037A and/or TPox037B cannot mediate the infection of HeLa cells.

Accordingly, based on this information, construction of synthetic K3 orthologs wherein the TPox037 C motif, for example, any of the 11 amino acids within the motif or any of the 4 amino acids responsible for the HeLa cell infectivity is varied can be carried out for generating synthetic K3 orthologs capable of conferring replication in different cell types. As will be appreciated by one of skill in the art, such K3 orthologs would have to be tested in different cell types because as shown in FIG. 2 and Table 1, there does not appear to be a discernable pattern for determining host cell permissiveness.

As will be appreciated by one of skill in the art, this allows for the design of recombinant viruses that will infect only certain or only specific cell types, as discussed herein.

According to another aspect of the invention, there is provided a method for generating a recombinant orthopoxvirus having altered host permissiveness comprising:

In an orthopoxvirus, replacing at least one native amino acid within domain C of the orthopoxvirus K3 protein as set forth in SEQ ID No: 12 with a non-native amino acid, thereby generating a recombinant orthopoxvirus;

transfecting a panel of possible host cell types with the recombinant orthopoxvirus; and detecting recombinant orthopoxvirus growth within each respective one possible host cell type, wherein recombinant orthopoxvirus growth within a respective one possible host cell type indicates that the respective one host cell type is a permissive host cell type for the recombinant orthopoxvirus.

As used herein, a "possible" host cell type is a host cell that may be a permissive host cell for the recombinant orthopoxvirus. As will be appreciated by one of skill in the art, any cell type of interest may be a possible host cell type and may be a member of the panel that is one type of host cell on the panel of possible host cell types.

In some embodiments, the method further comprises comparing the permissive host cell types from the panel to known host cell permissiveness of a control orthopoxvirus. In some embodiments, the control orthopoxvirus is the same type of orthopoxvirus as the recombinant orthopoxvirus. In some embodiments, the recombinant orthopoxvirus has altered host permissiveness if the permissive host cell types of the recombinant orthopoxvirus and the known permissive host cell types of the control orthopoxvirus are different.

Referring to FIG. 7A, the consensus sequence for Domain C is $X_1MHMX_2RYX_3X_4$ (SEQ ID No: 12), where $X_1$ is K or Q; $X_2$ is D or N; $X_3$ is V or F; and $X_4$ is E or K.

For example, as shown in FIG. 10, replacing K45 with E (SEQ ID No: 8) or T (SEQ ID No: 9) in vvWR causes it to replicate in sheep cells in addition to rodent cells). The "K" is highlighted in FIG. 9.

Similarly, replacing E53 with K (SEQ ID No: 10) in vvWR causes it to replicate in sheep cells in addition to rodent cells. The "E" is also highlighted in FIG. 9.

As shown in FIG. 11, replacing Y47 with H (SEQ ID No: 11) in Sheeppoxvirus 011 (SPPV011) causes it to lose the ability to replicate in human cells, monkey cells and pig cells while retaining the ability to replicate in sheep cells. The "Y" is highlighted in FIG. 9.

In some embodiments, the point mutation is K45E (SEQ ID No: 8), K45T (SEQ ID No: 9), E53K (SEQ ID No: 10) or Y47H (SEQ ID No: 11).

In other embodiments of the invention, there is provided an orthopoxvirus K3 protein consisting of the sequence as set forth in any one of SEQ ID Nos: 8-11.

As will be apparent to one of skill in the art, these gains and losses of function are based on laboratory observations and were not predictable because, as noted above, there is no discernable pattern for determining host cell permissiveness when swapping multiple, let alone single, amino-acids.

Specifically, it is highly surprising that three of these point mutations in vaccinia K3 (K3/K45E, K3/K45T and K3/E53K) gained the function of being able to replicate in sheep cells because the wild-type vaccinia K3 cannot replicate in sheep cells. For the sheeppoxvirus 011 mutation Y47H, it lost the function of being able to grow in Hela (human), Vero (monkey) and PK15 (pig) cells (the wild-type 011 protein could mediate the virus to grow in these cells) but retained the ability to replicate in sheep cells.

That is, one of skill in the art would expect that an amino acid change within this domain would at best have no effect or would result in a total loss of function. In contrast, three point mutations actually resulted in an increase in host cell permissiveness while one point mutation resulted in an orthopoxvirus that is specific for sheep cells.

As will be appreciated by one of skill in the art, there are uses which can be envisioned for which a wider host range may be preferred and uses which can be envisioned for which a narrower host range would be preferred or where a specific host range would be preferred.

As will be appreciated by one of skill in the art, the deletion of the E3L gene will make the recombinant virus extremely safe to use, since deletion of the E3L gene results in a vaccinia virus that is attenuated even in nude mice. For example, the deletion of the E3L gene makes the virus more effective in inducing immune response since vaccinia E3 protein inhibits many innate immune responses, such as the interferon response and the TNF-α response.

As will be apparent to one of skill in the art, the selection of the K3 ortholog can also be used to design recombinant viruses that can infect a number of hosts or can be specific for a single host, as can be discerned from Table 1 and FIG. 2. For example, using this selection system we can make a recombinant poxvirus, for example a vaccinia virus that only grows in pigs. The reason for this is when you want to immunize pigs, you wouldn't want other animals accidentally infected (including the people who do the immunization).

As discussed herein, the current understanding on poxvirus K3 family protein is that they act as pseudo-substrate for PKR, that is, the K3 protein inhibits the phosphorylation of the "real" cellular substrate, eIF2α, by providing an "alternative" or "viral" substrate instead of or along with the "real" or "cellular" substrate, eIF2α, thereby at least reducing phosphorylation of eIF2α.

As will be known to those of skill in the art, pseudo-substrates are typically poor choices for treatment, especially in the case of PKR, which carries out more functions within the cell than just phosphorylation of eIF2α, which reduces cellular protein synthesis. For example, PKR also phosphorylates the inhibitory subunit of $NF_KB$ Specifically, based on the belief that K3 acts as a pseudo-substrate for eIF2α phosphorylation, one of skill in the art would conclude that administering an effective amount of K3 to a cell would prevent translation inhibition but would have no effect on the other functions of PKR, for example, inhibition of $NF_KB$.

However, as discussed herein, poxvirus K3 proteins do not simply act as a pseudo-substrate of PKR, they actually mediate degradation of PKR. Thus, the poxvirus K3 peptides can be used as a therapeutic agent to degrade PKR in a disease in which PKR plays an enhancing role, that is, enhances severity of the disease, such as for example acute lymphocytic leukemia, acute myeloid leukemia, breast cancer, certain types of colon cancers, hepatocellular carcinoma, small-size peripheral adenocarcinoma of the lung, and hepatitis C virus induced liver cancer.

Specifically, the K3 proteins will accomplish at least one or more of the following: reduction of growth rate of cancerous cells, reduction of spread of cancerous cells, and reduction of tumor size compared to an untreated cancer of similar type. That is, administration of poxvirus K3 protein will reduce the severity and/or the duration of one or more symptoms associated with a PKR-enhancing disease. As discussed herein, these beneficial effects are the result of the K3-mediated degradation of PKR.

It is further noted that a clear link has been demonstrated between PKR and inflammation. Accordingly, in other embodiments of the invention, an effective amount of K3 protein is administered to reduce unwanted or excessive inflammation, for example, associated with chronic inflammation and/or autoimmune diseases.

According to another aspect of the invention, there is provided a method of treating a PKR-enhancing disease comprising administering to an individual in need of such treatment an effective amount of poxvirus K3 protein.

There is also provided poxvirus K3 protein for treating a PKR-enhancing disease.

There is also provided use of poxvirus K3 protein for treating a PKR-enhancing disease.

As used herein, a "PKR-enhancing disease" is any disease known or suspect of being made more severe by PKR activity. Suitable diseases and/or conditions include but are by no means limited to acute lymphocytic leukemia, acute myeloid leukemia, breast cancer, certain types of colon cancers, hepatocellular carcinoma, small-size peripheral adenocarcinoma of the lung, hepatitis C virus induced liver cancer and excess or unwanted inflammation.

As will be appreciated by one of skill in the art, "an individual in need of such treatment" in regard a PKR-enhancing disease is an individual who suffers from acute lymphocytic leukemia, acute myeloid leukemia, breast cancer, certain types of colon cancers, hepatocellular carcinoma, small-size peripheral adenocarcinoma of the lung, hepatitis C virus induced liver cancer or excess or unwanted inflammation.

In the examples shown in FIG. 8C, the method of the invention is used to express Lassa fever virus GP protein for use as a vaccine, and hepatitis E ORF2 protein and human herpesvirus 8 ORF51 proteins for use in diagnostic methods. As will be apparent to one of skill in the art, the fact that recombinant poxviruses comprising these diverse peptides can be generated demonstrates that the method of the invention can be used for the generation of recombinant viruses comprising any gene of interest.

As will be appreciated by one of skill in the art, as used herein, "gene of interest" does not necessarily include only "genes" in the traditional sense but may also include for example but by no means limited to peptide domains or peptide fragments or open reading frames or short artificial peptides.

As will be appreciated by one of skill in the art, any suitable poxvirus promoter may be used within the invention. Examples of suitable poxvirus promoters will be readily apparent to one of skill in the art and/or can be readily determined. Examples of suitable promoters include but are by no means limited to synthetic poxvirus early/late promoter, p11 promoter, and early promoter p7.5 and the like.

As will be appreciated by one of skill in the art, the recombinant virus can be used to express the gene of interest in specific cell types. While this can allow for a more targeted immune response and can also prevent cross-species migration of the virus particles, it can also be used to generate peptides that are more accurate representations of the "native" protein product of the gene of interest. For example, as will be known by those of skill in the art, bacterially-produced eukaryotic proteins often lack cell type-specific modifications and therefore may not assume an entirely accurate confirmation. This is overcome in the instant invention which permits for quick and easy expression of the product of a gene of interest in a suitable cell type.

Furthermore, although deletion of vaccinia K3L alone did not cause a noticeable change in the virus replication in all the cell lines tested (FIG. 2), it has been reported that the K3 protein is important for the virus to disseminate in mice (Rice et al., 2011, J. Virol., 85:550). As such, inhibition of the function of poxvirus K3 proteins will also compromise virus virulence.

Specifically, as shown herein, the NEDD8 activating enzyme (NAE) inhibitor MLN4924, can completely block poxvirus K3 mediated PKR degradation. Accordingly, this molecule and molecules related thereto can inhibit poxvirus replication in vivo.

The synthesis of MLN4924 is described in US Pat. No. 8,207,177, the contents of which are incorporated herein in their entirety for their disclosure on synthesis methods, chemical structure, preparation of pharmaceutical compounds and methods of use of MLN4924 and the related compounds.

According to another aspect of the invention, there is provided a method of treating a poxvirus infection comprising administering to an individual in need of such treatment an effective amount of a compound of formula (VIIIa):

(VIIIa)

or a pharmaceutically acceptable salt thereof, wherein:

stereochemical configurations depicted at asterisked positions indicate relative stereochemistry;

Q is $C(R^k)$;

$R^a$ is —OH;

$R^b$ is hydrogen, fluoro, or $C_{1-4}$ aliphatic;

$R^c$ is hydrogen, —OH, or —$OCH_3$;

$R^d$ is hydrogen;

$R^8$ is hydrogen or $C_{1-4}$ aliphatic;

$R^k$ is hydrogen;

each $R^P$ independently is fluoro; —$OR^{5x}$; —$N(R^{4x})(R^{4y})$; —$CO_2R^{5x}$; —$C(O)N(R^{4x})(R^{4y})$; $C_{1-4}$ aliphatic optionally substituted with —$OR^{5x}$, —$N(R^{4x})(R^{4y})$, —$CO_2R^{5x}$, or —$C(O)N(R^{4x})(R^{4y})$; or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$;

each $R^{8p}$ independently is fluoro; —$OR^{5x}$, —$N(R^{4x})(R^{4y})$; —$CO_2R^{5x}$; —$C(O)N(R^{4x})(R^{4y})$; $C_{1-4}$ aliphatic optionally substituted with —$OR^{5x}$, —$N(R^{4x})(R^{4y})$, —$CO_2R^{5x}$, or —$C(O)N(R^{4x})(R^{4y})$; or $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; provided that when two $R^{8p}$ are attached to the same carbon atom, one must be selected from the group consisting of fluoro; —$CO_2R^{5x}$; —$C(O)N(R^{4x})(R^{4y})$; $C_{1-4}$ aliphatic optionally substituted with —$OR^{5x}$, —$N(R^{4x})(R^{4y})$, $CO_2R^{5x}$, or —$C(O)N(R^{4x})(R^{4y})$; and $C_{1-4}$ fluoroaliphatic optionally substituted with —$OR^{5x}$, —$N(R^{4x})(R^{4y})$, —$CO_2R^{5x}$, or —$C(O)N(R^{4x})(R^{4y})$; or two $R^{8p}$ on the same carbon atom together form ═O or ═$C(R^{5x})_2$;

$R^{4x}$ is hydrogen, $C_{1-4}$ alkyl, $C_{1-4}$ fluoroalkyl, or $C_{6-10}$ ar($C_{1-4}$ )alkyl, the aryl portion of which is optionally substituted;

$R^{4y}$ is hydrogen; $C_{1-4}$ alkyl; $C_{1-4}$ fluoroalkyl; $C_{6-10}$ ar($C_{1-4}$ )alkyl, the aryl portion of which is optionally substituted; optionally substituted 5- or 6-membered aryl; optionally substituted heteroaryl; or optionally substituted heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from the group consisting of N, O, and S;

each $R^{5x}$ independently is hydrogen, $C_{1-4}$ alkyl, $C_{1-4}$ fluoroalkyl, or an optionally substituted $C_{6-10}$ aryl, or optionally substituted $C_{6-10}$ ar($C_{1-4}$ )alkyl;

wherein:

in each recitation of optionally substituted aryl, the aryl group, when substituted, contains on one or more unsaturated carbon atoms a substituent independently selected from the group consisting of halo, —$NO_2$, —CN, —R*, —C(R*)═C(R*)$_2$, —C≡C—R*, —OR*, —$SR^o$, —$S(O)R^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^*$, —OC(O)$N(R^+)_2$, —O—C(O)R*, —$CO_2R^*$, —C(O)—C(O)R*, —C(O)R*, —C(O)$N(R^+)_2$, —C(═$NR^+$)—$N(R^+)_2$, —C(═$NR^+$) —OR*, —$N(R^+)$—$N(R^+)_2$, —$N(R^+)$C(═$NR^+$)—$N(R^+)_2$, —$NR^+SO_2R^o$, —$NR^+SO_2N(R^+)_2$, —P(O)(R*)$_2$, —P(O)(OR*)$_2$, —O—P(O)—OR*, and —P(O)($NR^+$)—$N(R^+)_2$;

in each recitation of optionally substituted heteroaryl, the heteroaryl group, when substituted, if on an unsaturated carbon atom, contains on one or more unsaturated carbon atoms, a substituent independently selected from the group consisting of halo, —$NO_2$, —CN, —R*, —C(R*)═C(R*)$_2$, —C≡C—R*, —OR*, —$SR^o$, —$S(O)R^o$, —$SO_2R^o$, —$SO_2N(R^+)_2$, —$N(R^+)_2$, —$NR^+C(O)R^*$, —$NR^+C(O)N(R^+)_2$, —$NR^+CO_2R^o$, —O—$CO_2R^*$, —OC(O)$N(R^+)_2$, —O—C(O)R*, —$CO_2R^*$, —C(O)—C(O)R*, —C(O)R*, —C(O)N (R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R°, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, contains on one or more substitutable nitrogen atoms, a substituent independently selected from the group consisting of —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; and in each recitation of optionally substituted heterocyclyl, the heterocyclyl group, when substituted, if on a saturated carbon atom, contains on one or more saturated carbon atoms, a substituent independently selected from the group consisting of halo, —NO$_2$, —CN, —R*, —C(R*)=C(R*)$_2$, —C≡C—R*, —OR*, —SR°, —S(O)R°, —SO$_2$R°, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R°, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R°, =N—NHSO$_2$R°, and =N—R*, and, if on a substitutable nitrogen atom, contains on one or more substitutable nitrogen atoms, a substituent independently selected from the group consisting of —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R° is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms independently selected from the group consisting of N, O, and S; and each occurrence of R* is independently hydrogen, aliphatic, aryl, heteroaryl, or heterocyclyl group;

s is 0, 1, or 2; and t is 0, 1, or 2.

As will be appreciated by one skill in the art, an "individual in need of such treatment" may be an individual who is suspected of being infected or is known to be infected by a poxvirus.

As will be appreciated by one of skill in the art, MLN4924 and its related compounds can be used to treat any poxvirus infection provided that the poxvirus has a K3 ortholog. Consequently, MLN4924 and its related compounds may be used to treat sheeppox virus infection, as well as many orthopoxvirus infections, for example but by no means limited to camelpox and variola (the causative virus for smallpox).

As such, the individual in need of such treatment is an animal that has been infected by an orthopoxvirus, for example, a human, a sheep, a monkey, a camel, a mouse and the like.

Also provided is the use of the compound as discussed above for treating a poxvirus infection.

Also provided is any one of the compounds discussed above for treating a poxvirus infection.

In some embodiments, the compound is MLN4924.

As will be appreciated by one of skill in the art, treatment of an individual infected with a poxvirus or suffering from a poxvirus infection will accomplish at least one or more of the following: reduce poxvirus-mediated degradation of PKR, increase or improve host immune response to the poxvirus, and reduce the severity of one or more symptoms associated with a poxvirus infection, for example, fever, headache, muscle aches and feelings of exhaustion.

The invention will now be further explained and elucidated by way of examples; however, the invention is not necessarily limited to the examples.

EXAMPLE 1

Recombinant Virus Construction

Figure 1:
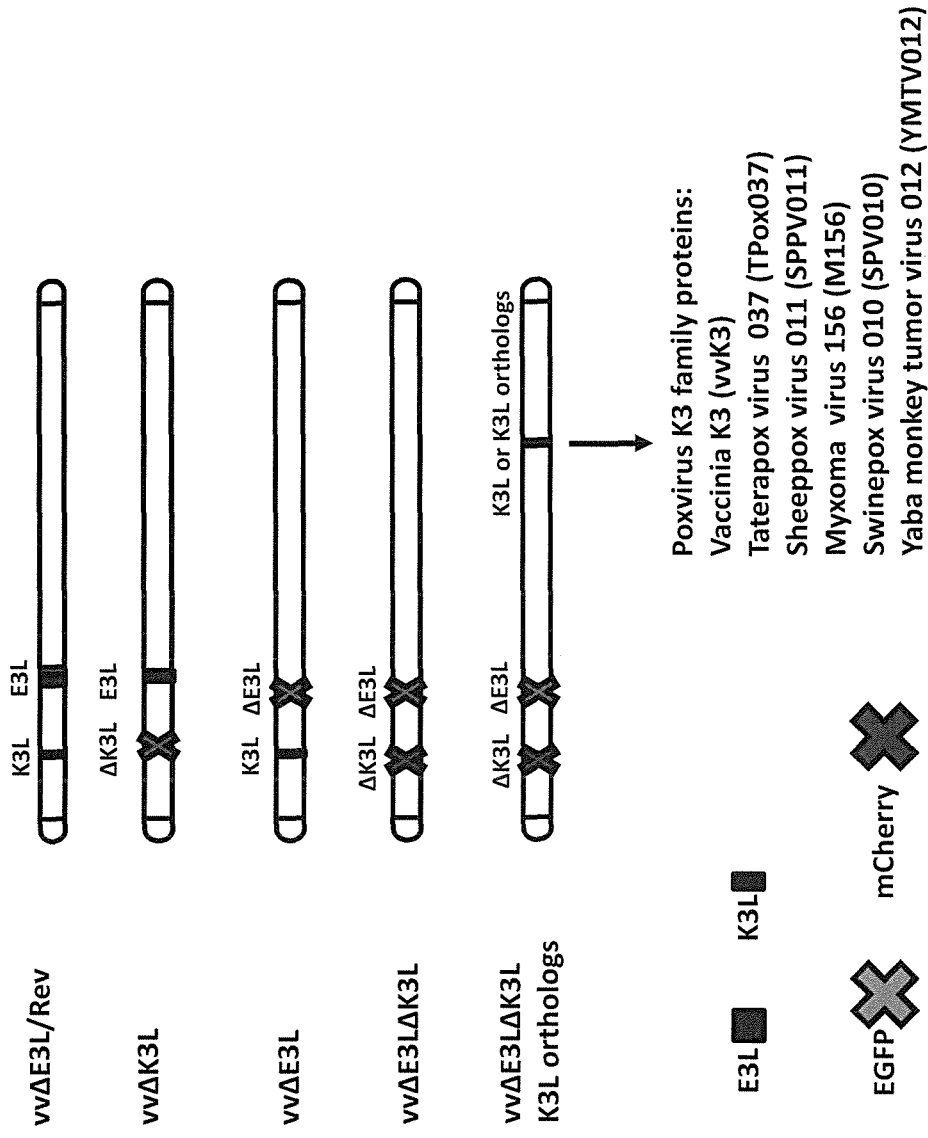
FIG. 1. Schematic representation of recombinant vaccinia viruses used herein. 1) VVΔE3L/Rev: vaccinia E3L deletion revertant virus in which the E3L gene was inserted back into the deletion virus; 2) VVΔK3L: the K3L gene was disrupted by insertion of the EGFP fluorescence protein gene; 3) VVΔE3L: the E3L gene was disrupted by insertion of EGFP florescence protein gene; 4) VVΔE3LΔK3L; the K3L was disrupted by insertion of mCherry and the E3L by EGFP genes; 5) VVΔE3LΔK3L/K3orthologs: a variety of poxvirus K3 orthologs (as shown in the figure) driven by vaccinia K3L promoter inserted back into the VVΔE3LΔK3L virus in the A45R locus (nonessential for the virus in vitro and in vivo).

All the recombinant viruses discussed herein are shown in FIG. 1. Using standard homologous recombination technique, we disrupted the E3L (VVΔE3L) and K3L (VVΔK3L) genes individually by the insertion of EGFP gene into the wild-type vaccinia Western Reserve virus (vvWR) using BHK 21 cells. Based on the VVΔE3L, we further disrupted the K3L gene and created an E3L and K3L double deletion mutant (VVΔE3LΔK3L) using a human cell HeLa PKR deletion cell line. Based on the VVΔE3LΔK3L, K3 orthologs from six different poxviruses, including vaccinia K3, taterapox virus 037 (TPox037), sheeppox virus 011 (SPPV011), Myxoma virus 156 (M156), swinepox virus 010 (SPV010) and Yaba monkey tumor virus 012 (YMTV012), were inserted into vaccinia A45R locus (non-essential for the virus both in vitro and in vivo) under the control of vaccinia K3L promoter. The selection of the recombinant vaccinia virus (VVΔE3LΔK3L/K3ortholog) was done in the cell lines as follows: BHK21 (baby hamster kidney) for vaccinia K3 and TPox037, OA3.Ts (sheep testis) for SPPV011, RK13 (rabbit kidney) for M156, PK15 (pig kidney) for SPV010 and CV-1 (African green monkey kidney) for YMTV012. The expression of the five poxvirus K3 orthologs was confirmed by RT-PCR.

EXAMPLE 2

Replication of the Recombinant Vaccinia Viruses Expressing Poxvirus K3 Orthologs The replication of the VVΔE3LΔK3L viruses expressing poxvirus K3 orthologs was examined in cell lines derived from seven different animal species: HeLa (human), BHK21 (hamster), NIH/3T3 (mouse), CV-1 (monkey), RK13 (rabbit), OA3.Ts (sheep) and PK15 (pig). As shown in FIG. 2, the wild-type vaccinia virus (expressing EGFP) and vvΔK3L replicated in all the cell lines tested. Furthermore, all the viruses replicate in the HeLa cells, in which the PKR gene was disrupted (HeLa/PKRko). The double deletion mutant (VVΔE3LΔK3L) could only replicate in HeLa/PKRko cells. Vaccinia K3 and its orthopoxvirus ortholog TPoxO37 could restore the replication of VVΔE3L in RK13 and the two rodent cell lines (BHK21 and 3T3), while TPox037, but not vaccinia K3, could mediate the virus to grow in HeLa, OA3.Ts and PK15 cells (FIG. 2). The K3 orthologs from four highly host restrictive poxviruses (sheeppoxvirus/sheep, myxoma/rabbit, swinepoxvirus/pig, YMTV/monkey) could restore the replication of VVΔE3LΔK3L in their corresponding host cells: 1)

Figure 3:
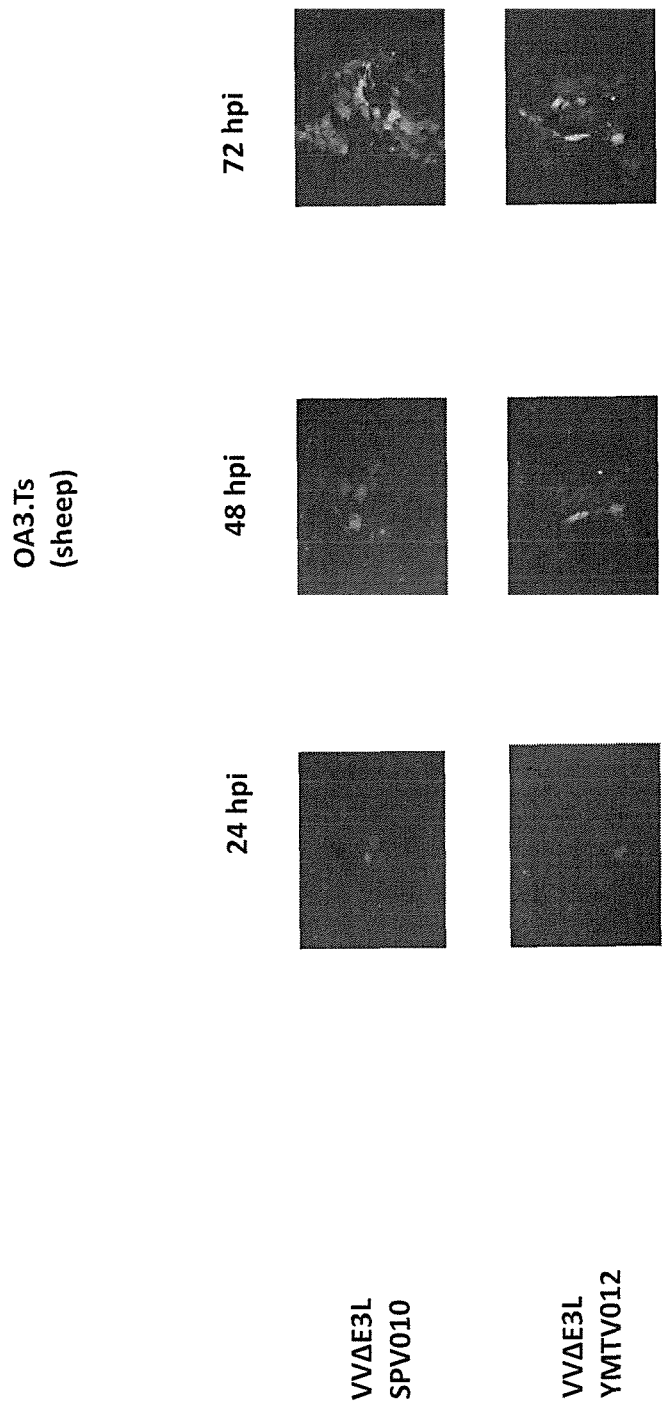

VVΔE3L/SPPV011 replicates in OA3.Ts cells; 2) VVΔE3L/M156 replicates in RK13 cells; 3) VVΔE3L/SPV010 replicates in PK15 cells; 4) VVΔE3L/YMTV012 replicates in CV-1 cells (FIG. 2). The SPPV011 mediate the virus replication in all other cell types with the exception of the two rodent cell lines (BHK21 and 3T3). In addition to their respective host cells, the YMTV could mediate the virus to grow in human HeLa cells and a slow replication phenotype in OA3.Ts cells; while the SPV010 mediated the slow replication phenotype in OA3.Ts cells (FIG. 3). The host cell specificities mediated by poxvirus K3 orthologs were summarized in Table 1. As can be seen, different host ranges can be conferred by different K3 orthologs.

EXAMPLE 3

Poxvirus K3 Orthologs Mediated PKR Degradation Through Neddylation Dependent Pathway Since poxvirus K3 family proteins share important amino acid sequence homology with eukaryotic initiation factor 2α (eIF2α) (which is a substrate for protein kinase R (PKR)), it has been assumed that poxvirus K3 proteins inhibit PKR function by acting as a pseudo-substrate for PKR. However, as discussed herein, it has been demonstrated that this is not correct.

The effect on PKR activation by the three poxvirus K3 proteins able to mediate the virus replication in human cells (HeLa) as shown in FIG. 2, was investigated. HeLa cells were investigated with the selected virus at a high multiplicity of infection (moi) of 10 and the cell lysate was collected at several time points, 3, 6, 12 and 24 hours post infection (hpi). Significant PKR phosphorylation was observed after 6 hpi in the cells infected with the double knockout virus (vvΔE3LΔK3L) and E3L single knockout virus (vvΔE3L expressing K3). By 24 hpi, even the wild-type virus (with both E3L and K3L genes) induced significant PKR phosphorylation. However, in the cells infected with the virus expressing SPPV011, TPox037 or YMTV012, the quantity of PKR was drastically reduced at 6 hpi and almost non-detectable after 12 hpi (FIG. 4A).

The non-structural proteins (NSs) of Rift Valley fever virus (a bunyavirus) has been reported to mediate PKR degradation regulated by SKP1-Cul1-F-Box E3 ligase complex, which is activated by a ubiquitin like protein called NEDD8 (PLOS PAthogene 2016, Mudhasani et al). The process of adding NEDD8 to the target protein is called neddylation. A highly specific small molecule inhibitor of NEDD8 activating enzyme (NAE), called MLN4924 (developed by Millennium Pharmaceuticals), can block the degradation of PKR. Here, we investigated if the degradation of PKR mediated by poxvirus K3 family proteins could also be blocked by MLN4924. HeLa cells were infected with the viruses as in FIG. 4A, but in the presence of 10 μM MLN4924. As shown in FIG. 4B, the level of phosphorylated PKR in the cells infected with recombinant viruses expressing the three poxvirus K3 proteins (SPPV011, TPox037 and YMTV012) is comparable to the cells infected with vvΔE3LΔK3L and vvΔE3L. Therefore, MLN4924 completely blocked the degradation of PKR. As will be apparent to one of skill in the art, K3 is not an alternate substrate but is in fact targeting PKR for degradation. As such, without the knowledge that K3 is involved in neddylation, it was impossible to predict that MLN4924 would be useful as a treatment for a poxvirus infection.

EXAMPLE 4

MLN4924 Inhibit vvΔE3L Expressing SPPV011, TPox037 or YMTV012 Replication in HeLa Cells, but not in HeLa/PKRko Cells Since MLN4924 blocked poxvirus K3 protein mediated PKR degradation and PKR is the key antiviral effector in the suppression of vvΔE3L replication in HeLa cells, MLN4924 will mediate inhibition of the replication of the virus vvΔE3L/SPPV011, TPox037 or YMTV012 in HeLa cells. HeLa cells were infected with the viruses as shown in FIG. 4 with and without the presence of 10 μM MLN4924. A 5 hpi virus sample was collected and used as the baseline for comparing virus titres. As shown in FIG. 5A, all the viruses replicated comparably well in HeLa/PKRko cells with or without the presence of MLN4924. In HeLa cells (FIG. 5B), the double knockout virus vvΔE3LΔK3L and vvΔE3LΔK3L (with K3L) cannot replicate as there is no increase in the virus titre between 5 hpi and 48 hpi. In contrast, the other viruses (vvWRwt, vvΔE3L/SPPV011, TPox037 and YMTV012) replicate efficiently in HeLa cells with over 10 fold increase in their titre after 48 hpi in comparison with the 5 hpi. In the presence of MLN4924, replication of the virus (vvΔE3L/SPPV011, TPox037 and YMTV012, all of which have the E3L deleted and K3L replaced with other poxvirus K3 orthologs) was inhibited by over 10 fold, while the wild-type virus (vvWRwt) grew almost equally well as without the drug. Thus, the replication in HeLa cells mediated through the poxvirus K3 orthologs were blocked by the neddylation inhibitor MLN4924.

Next, we examined the inhibition of the virus replication by MLN4924 using different doses, ranging from 0 μM to 10 μM (5 fold dilution). At the concentration of 10 μM and 2 μM, vvΔE3L/TPox037 and YMTV012 were inhibited most. At the same concentration, vvΔE3L/SPPV011 is more resistant in comparison to Tpox037 and YMTV012 recombinant virus (FIG. 6A). At the concentration between 0.08 and 0 μM, no detectable inhibition was observed. In addition, the inhibition of PKR degradation was also examined with the same range of MLN4924 doses. As shown in FIG. 6B, the degree of inhibition of the virus replication correlates well with the degree of inhibition of PKR degradation. Thus, the neddylation inhibitor MLN4924 demonstrated a dose-dependent inhibition of the virus replication and PKR degradation. This confirms that the inhibition of PKR degradation is the reason why MLN4924 inhibits the virus replication.

EXAMPLE 5

Identification of a K3 Protein Motif Critical for Mediating PKR Degradation

Figure 7B:
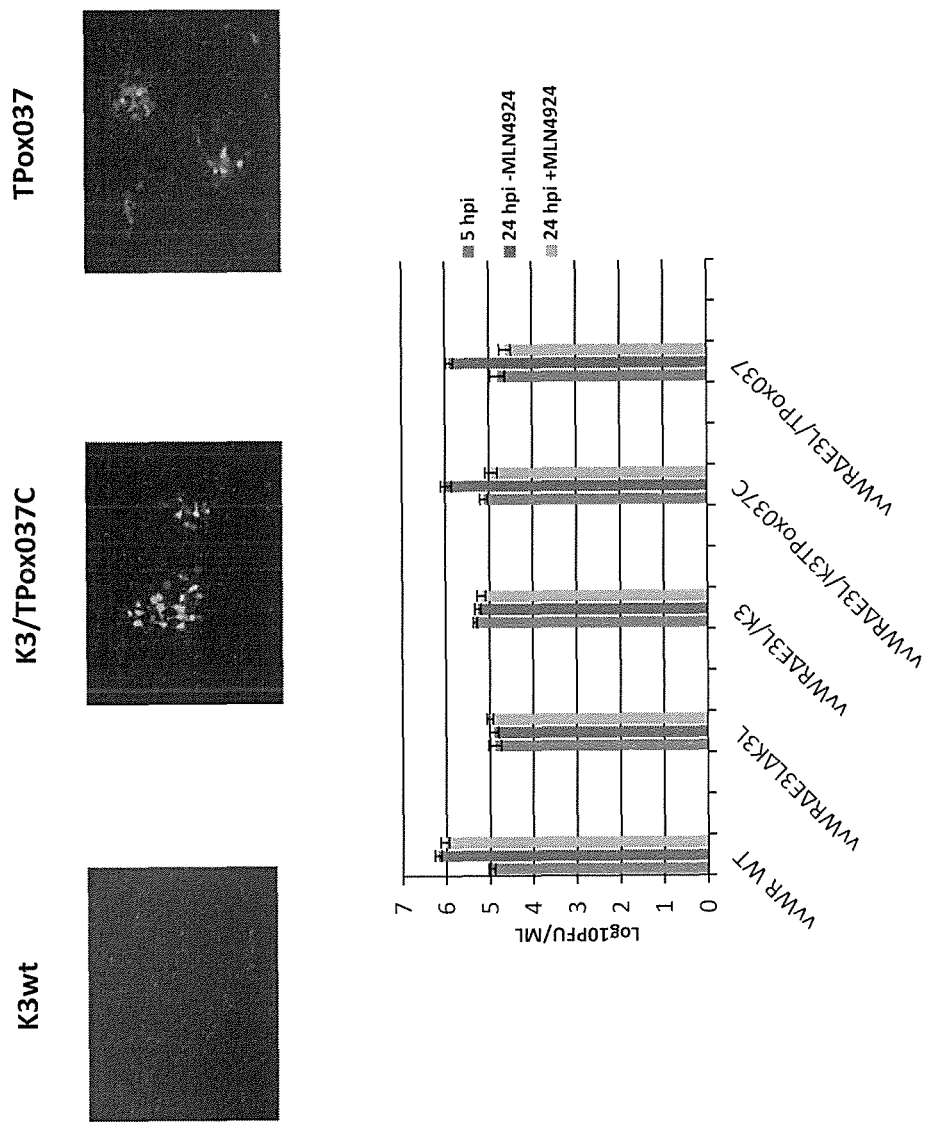
Figure 7C:
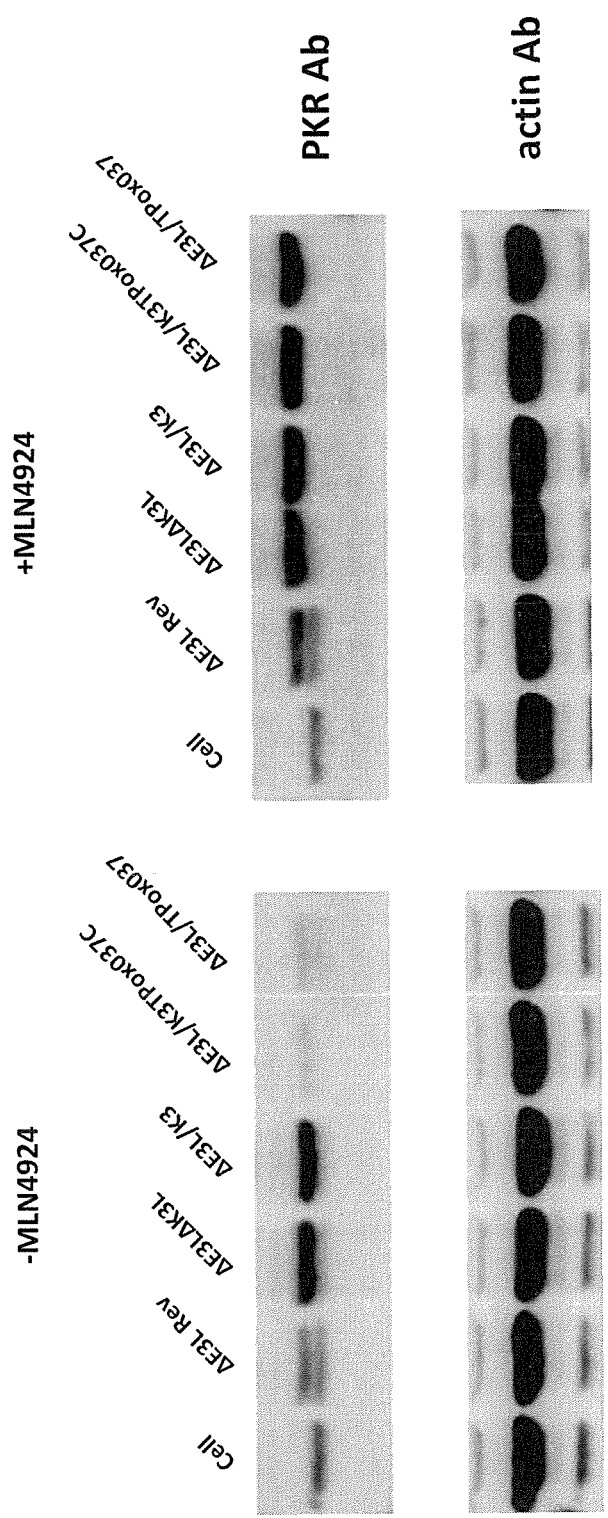

Both vaccinia and taterapoxviruses are orthopoxvirus. Vaccinia K3 protein and its taterapoxvirus ortholog, TPox037, are highly conserved. As illustrated in FIG. 7A, there is only 11 amino acid variation between the two and these 11 amino acids can be grouped in three loci: TPox037A, TPox037B, and TPox037C. Using vaccinia K3 as the backbone, three chimeric constructs bearing TPox037 motif A, B or C were made (termed as K3/TPox037A, K3/TPox037B and K3/TPox037C) and transfected into HeLa/PKRko cells infected with vvΔE3L. It was expected that the homologous recombination would happen between the wild-type K3L gene of vvΔE3L and the transfected chimeric DNA (K3/TPox037A, K3/TPox037B and K3/TPox037C). To test if the chimeric constructs of vaccinia K3 and taterapoxvirus 037 can mediate vvΔE3L replication in HeLa cells, the total virus collected from above infection (with vvΔE3L) and transfection (with K3/TPox037A, K3/TPox037B and K3/TPox037C) was passaged in HeLa cells. As shown in FIG. 7B, only the chimeric K3/TPox037C restored vvΔE3L replication in HeLa cells. The K3/TPox037 chimeric protein mediated similar growth rate and PKR degradation as TPox037, which can be blocked by the presence of MLN4924 (FIG. 7B and 7C). Thus, the motif TPox037 C is critical for the biological function of vaccinia K3 and TPox037 of mediating degradation of PKR. This demonstrates that the motif called TPox037 is critical for mediating PKR degradation in HeLa cells, or the interaction of human PKR with K3 and K3 othologs.

EXAMPLE 6

Application of Poxvirus K3 Proteins as Selection Marker for Making Recombinant Vaccinia Viruses While vaccinia virus has a very broad range of host cells, the double deletion mutant vaccinia virus, vvWRΔE3LΔK3L, can only replicate in HeLa/PKRko cells (FIG. 2). Based on vvWRΔE3LΔK3L, we can create recombinant vaccinia viruses with different host specificity by expressing different poxvirus K3 orthologs (FIG. 2). Here, we use the TPox037 as an example to demonstrate that poxvirus K3 ortholog proteins can be used as positive selection markers to generate recombinant vaccinia viruses for expression of foreign proteins.

Figure 8A:
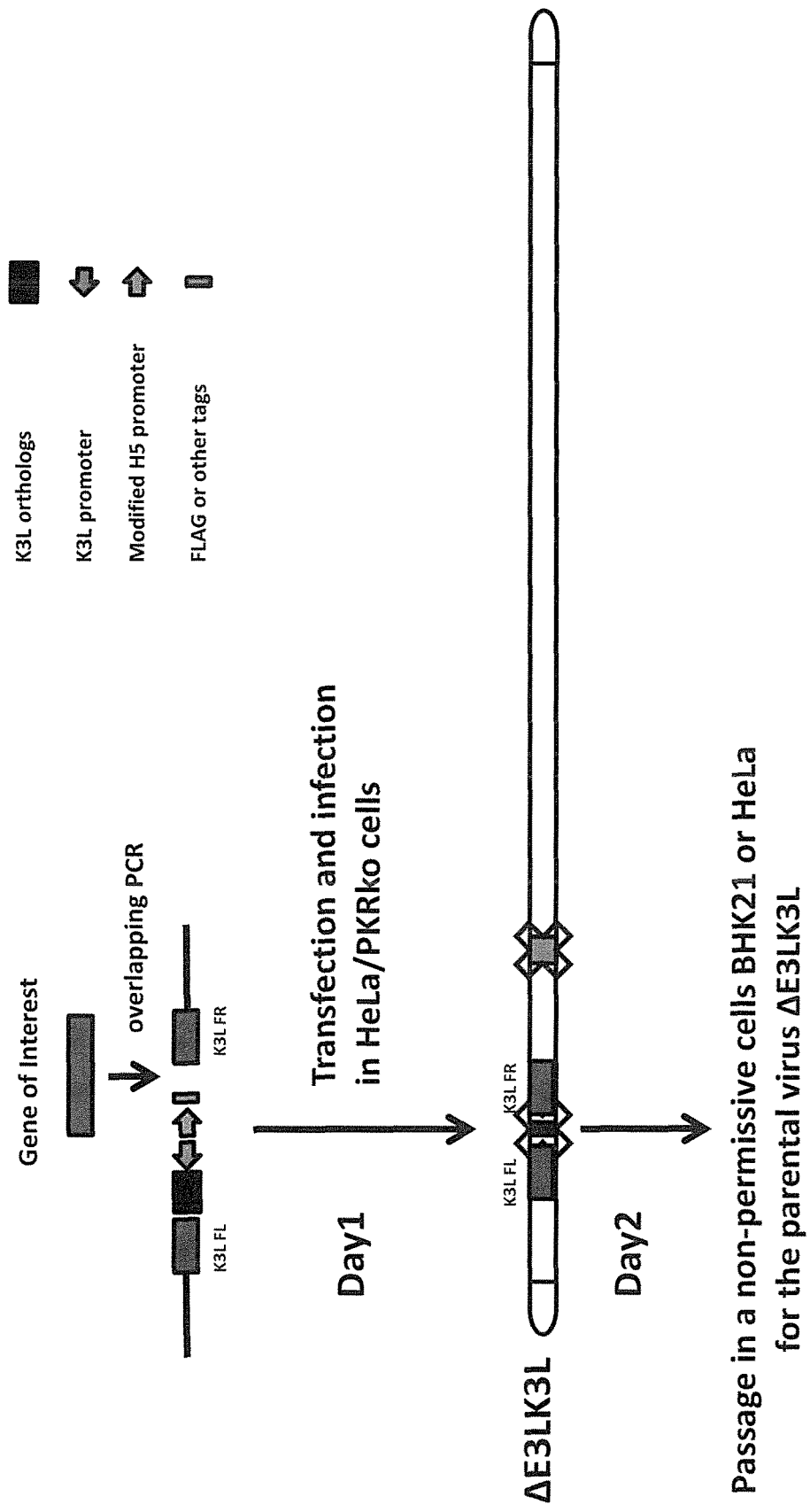

As illustrated in FIG. 8A, a backbone of the recombinant vector consists of two flanking regions of vaccinia K3L gene (K3L FL and FR), Tpox037 gene (or any other poxvirus K3 orthologs) driven by SPPV011 promoter, and the modified vaccinia H5 promoter. The foreign gene of interest can be inserted and fused with a FLAG tag (or other tags of the choice) either at the N- or C-terminus downstream of the H5 promoter using polymerase chain reaction (PCR) with primer pairs overlapping with the adjacent loci in the backbone of the recombinant vector. The construction of the recombinant vector with a foreign gene to express can be done between 3 to 5 hours. In the same day (Day1), the recombinant vector can be transfected into HeLa/PKRko cells infected with the vvWRΔE3LΔK3L virus (which only replicates in HeLa/PKRko cells). On day 2, the virus can be collected and passaged into non-permissive cells for the parental virus vvWRΔE3LΔK3L but permissive for the recombinant virus carrying the poxvirus K3 ortholog gene (in this case Tpox037). In the example shown in the FIG. 8, the TPox037 can mediate the recombinant virus to replicate in BHK21 or HeLa cells. Three rounds of amplification passages can be achieved between day 3 and day 6 (FIG. 8B). The recombinant virus amplified from the third passage (on day 6) can be used to detect the protein expression. Using this procedure shown in FIG. 8, we have made 4 recombinant viruses expressing Lassa fever virus GP protein (for vaccine development), human hepatitis E virus ORF2 protein (for diagnostic assay), rat hepatitis E ORF2 protein (for diagnostic assay) and human herpes virus type 8 ORF51 protein (for diagnostic assay). Thus, recombinant vaccinia virus can be produced using a poxvirus K3 as a positive selection marker. In the case of using TPox037, this can be done within 6 days.

The scope of the claims should not be limited by the preferred embodiments set forth in the examples but should be given the broadest interpretation consistent with the description as a whole.

TABLE 1

Host specificity mediated by poxvirus K3 proteins

|  | Hela/PKRko (human) | Hela (human) | BHK2 (hamster) | 3T3 (mouse) | CV-1 (monkey) | RK13 (rabbit) | OA3.Ts (sheep) | PK15 (pig) |
| --- | --- | --- | --- | --- | --- | --- | --- | --- |
| vvΔE3L/Rev | + | + | + | + | + | + | + | + |
| vvΔK3L | + | + | + | + | + | + | + | + |
| vvΔE3LΔK3L | + | − | − | − | − | − | − | − |
| vvΔE3L/K3 | + | − | + | + | − | + | − | − |
| vvΔE3L/TPox037 | + | + | + | + | − | + | + | + |
| vvΔE3L/SPPV014 | + | + | − | − | + | + | + | + |
| vvΔE3L/M156 | + | − | − | − | − | + | − | − |
| vvΔE3L/SPV010 | + | − | − | − | − | − | +/− | + |
| vvΔE3L/YMTV012 | + | + | − | − | − | − | +/− | − |

The invention claimed is:

1. A method of preparing a recombinant poxvirus comprising;

providing a host cell comprising a parent poxvirus in which the coding sequences for native poxvirus E3 and K3 proteins have been disrupted or deleted, said host cell being pemlissive for growth of the parent poxvirus;

introducing an insertion cassette for inserting a gene of interest into the parent poxvirus genome at an insertion site into the host cell, said insertion cassette comprising a first crossover region, an expression cassette and a second crossover region, wherein the first crossover region has sufficient homology to an upstream region of the parent poxvirus genome that is upstream of the insertion site to initiate a crossover event with the parent poxvirus genome; the second crossover region has sufficient homology to a downstream region of the parent poxvirus genome that is downstream of the insertion site to initiate a crossover event with the parent poxvirus genome; and the insertion cassette comprises a first poxvirus promoter operably linked to a K3 ortholog for expression of the K3 ortholog from the first poxvirus promoter and a second poxvirus promoter operably linked to a gene of interest for expression of the gene of interest from the second poxvirus promoter;

subjecting the host cell to conditions permitting crossover events to occur between the insertion cassette and the parent poxvirus genome, subjecting the host cell to conditions suitable for generating a population of poxvirus particles, said population comprising parent poxvirus virus particles and recombinant poxvirus particles;

introducing said population into a second cell line non-permissive fix growth of the parent poxvirus but permissive for growth of the recombinant poxvirus;

subjecting the second cell line to conditions promoting production of recombinant virus particles; and recovering the recombinant virus particles.

2. The method according to claim 1 wherein the insertion cassette comprises, in sequence, the first crossover reion, the expression cassette and the second crossover region.

3. The method according to claim 1 wherein the insertion site is within or proximal to the deleted or disrupted K3 gene.

4. The method according to claim 3 wherein the first crossover region corresponds to a region of K3L FL and the second crossover region corresponds to K3L RL.

5. The method according to claim 1 wherein the first crossover region and the second crossover region respectively are at least 50 base pairs long.

6. The method according to claim 1 wherein the first crossover region has at least 95% identity to the poxvirus genome sequence.

7. The method according to claim 1 wherein the second crossover region has at least 95% identity to the poxvirus genome sequence.

8. The method according to claim 1 wherein the expression cassette comprises more than one gene of interest.

9. The method according to claim 1 wherein the recombinant poxvirus and/or the parent poxvirus is a vaccinia virus.

10. The method according to clam 1 wherein the expression cassette comprises an expression detector.

11. The method according to claim 1 wherein the K3 ortholog is selected from the group consisting of: taterapox virus. (an orthopoxvirus) 037 (TPox037); sheeppox virus orthologs 011 (SPPV011); Yana monkey tumor virus 012 (YMTV012); suipoxvirus 010 (SPV010); myxomavirus 156 (M156); vaccinia K3; and a synthetic or artificial K3 peptide that is permissive for growth in a cell line suitable for generating a population of parent poxvirus particles and recombinant poxvirus particles, but is only permissive for growth of the recombinant poxvirus in a second cell line.

12. A method of determining if a compound treats a poxvirus infection comprising administering to an animal that has been infected by a poxvirus an effective amount of a compound of formula (VIIIa):

(VIIIa)

or a pharmaceutically acceptable salt thereof, wherein:

stereochemical configurations depicted at asterisked positions indicate relative stereochemistry;

Q is $C(R^k)$;

$R^a$ is —OH;

$R^b$ is hydrogen, fluoro, or $C_{1-4}$ aliphatic;

$R^c$ is hydrogen, —OH, or —OCH$_3$;

$R^d$ is hydrogen;

$R^8$ is hydrogen or $C_{1-4}$ aliphatic;

$R^k$ is hydrogen;

each $R^p$ independently is fluoro; —OR$^{5x}$; —N(R$^{4x}$)(R$^{4y}$); —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), —CO$_2$R$^{5x}$, or —C(O)N(R$^{4x}$)(R$^{4y}$); or $C_{1-4}$ fluoroaliphatic optionally substituted with —OR$^{5x}$, —N(R$^{4x}$)(R$^{4y}$), —CO$_2$R$^{5x}$, or —C(O)N(R$^{4x}$)(R$^{4y}$);

each $R^{8p}$ independently is fluoro; —OR$^{5x}$, —N(R$^{4x}$)(R$^{4y}$); —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), —CO$_2$R$^{5x}$, or —C(O)N(R$^{4x}$)(R$^{4y}$); or $C_{1-4}$ fluoroaliphatic optionally substituted with —OR$^{5x}$, —N(R$^{4x}$) (R$^{4y}$), —CO$_2$R$^{5x}$, or —C(O)N(R$^{4x}$)(R$^{4y}$); provided that when two $R^{8p}$ are attached to the same carbon atom, one must be selected from the group consisting of fluoro; —CO$_2$R$^{5x}$; —C(O)N(R$^{4x}$)(R$^{4y}$); $C_{1-4}$ aliphatic optionally substituted with —OR$^{5x}$, —N(R$^{4x}$)(R$^{4y}$), CO$_2$R$^{5x}$, or —C(O)N(R$^{4x}$)(R$^{4y}$); and $C_{1-4}$ fluoroaliphatic optionally substituted with —OR$^{5x}$, —N(R$^{4x}$) (R$^{4y}$), —CO$_2$R$^{5x}$, or —C(O)N(R$^{4x}$)(R$^{4y}$); or two $R^{8p}$ on the same carbon atom together form =O or =C(R$^{5x}$)$_2$;

$R^{4x}$ is hydrogen, $C_{1-4}$ alkyl, $C_{1-4}$ fluoroalkyl, or $C_{6-10}$ ar($C_{1-4}$)alkyl, the aryl portion of which is optionally substituted;

$R^{4y}$ is hydrogen; $C_{1-4}$ alkyl; $C_{1-4}$ fluoroalkyl; $C_{6-10}$ ar($C_{1-4}$)alkyl, the aryl portion of which is optionally substituted; optionally substituted 5- or 6-membered aryl; optionally substituted heteroaryl; or optionally substituted heterocyclyl ring; or $R^{4x}$ and $R^{4y}$, taken together with the nitrogen atom to which they are attached, form an optionally substituted 4- to 8-membered heterocyclyl ring having, in addition to the nitrogen atom, 0-2 ring heteroatoms independently selected from the group consisting of N, O, and S;

each $R^{5x}$ independently is hydrogen, $C_{1-4}$ alkyl, $C_{1-4}$ fluoroalkyl, or an optionally substituted $C_{6-10}$ aryl, or optionally substituted $C_{6-10}$ ar($C_{1-4}$)alkyl;

wherein:

in each recitation of optionally substituted aryl, the aryl group, when substituted, contains on one or more unsaturated carbon atoms a substituent independently selected from the group consisting of halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$;

in each recitation of optionally substituted heteroaryl, the heteroaryl group, when substituted, if on an unsaturated carbon atom, contains on one or more unsaturated carbon atoms, a substituent independently selected from the group consisting of halo, —NO$_2$, —CN, —R*, —C(R*)=C(R*)$_2$, —C≡C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, and, if on a substitutable nitrogen atom, contains on one or more substitutable nitrogen atoms, a substituent independently selected from the group consisting of —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; and in each recitation of optionally substituted heterocyclyl, the heterocyclyl group, when substituted, if on a saturated carbon atom, contains on one or more saturated carbon atoms, a substituent independently selected from the group consisting of halo, —NO$_2$, —CN, —R*, C(R*)=C(R*)$_2$, —C≡—C—R*, —OR*, —SR$^o$, —S(O)R$^o$, —SO$_2$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$, =O, =S, =C(R*)$_2$, =N—N(R$^+$)$_2$, =N—OR*, =N—NHC(O)R*, =N—NHCO$_2$R$^o$, =N—NHSO$_2$R$^o$, and =N—R*, and, if on a substitutable nitrogen atom, contains on one or more substitutable nitrogen atoms, a substituent independently selected from the group consisting of —R*, —N(R*)$_2$, —C(O)R*, —CO$_2$R*, —C(O)—C(O)R*, —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*;

wherein:

each occurrence of R$^o$ is independently an aliphatic or aryl group;

each occurrence of R$^+$ is independently hydrogen or an aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms independently selected from the group consisting of N, O, and S; and each occurrence of R* is independently hydrogen, aliphatic, aryl, heteroaryl, or heterocyclyl group;

s is 0, 1, or 2; and t is 0, 1, or 2.

wherein the compound treats the poxvirus infection by accomplishing one or more of the following: reducing poxvirus-mediated degradation of PKR; increasing or improving the animal's immune response to the poxvirus; and reducing severity of one or more symptoms associated with a poxvirus infection in the animal.

13. A method for generating recombinant orthopox virus having altered host permissiveness comprising:

in an orthopoxvirus, replacing at least one native amino acid within domain C of the orthopoxvirus K3 protein as set forth in SEQ ID No: 12 with a non-native amino acid, thereby generating a recombinant orthopox virus;

transfecting a panel of possible host cell types with the recombinant orthopoxvirus; and detecting recombinant orthopoxrus growth within each respective one possible host cell type, wherein recombinant orthopoxvirus growth within a respective one possible host cell type indicates that the respective one host cell type is a permissive host cell type for the recombinant orthopoxvirus.

14. The method according to claim 13 further comprising comparing the permissive host cell types from the panel to known host cell permissiveness of a control orthopoxvirus.

15. The method according to claim 14 wherein tha recombinant orthopoxvirus has altered host permissiveness if the permissive host cell types o the recombinant orthopox virus and the known permissive host cell types of the control orthopoxvirus are different.

\* \* \* \* \*

SEQUENCE LISTING

<160> NUMBER OF SEQ ID NOS: 13

<210> SEQ ID NO 1
<211> LENGTH: 94
<212> TYPE: PRT
<213> ORGANISM: Human

<400> SEQUENCE: 1

Met Pro Gly Leu Ser Cys Arg Phe Tyr Gln His Lys Phe Pro Glu Val
1               5                   10                  15

Glu Asp Val Val Met Val Asn Val Arg Ser Ile Ala Glu Met Gly Ala
                20                  25                  30

Tyr Val Ser Leu Leu Glu Tyr Asn Ile Glu Met Ile Leu Leu
         35                  40              45

Ser Glu Leu Ser Arg Arg Ile Arg Ser Ile Asn Lys Leu Ile Arg
 50                  55                  60

Ile Gly Arg Asn Glu Cys Val Val Ile Arg Val Asp Lys Glu Lys
65                  70                  75                  80

Gly Tyr Ile Asp Leu Ser Lys Arg Arg Val Ser Pro Glu Glu
                 85                  90

<210> SEQ ID NO 2
<211> LENGTH: 88
<212> TYPE: PRT
<213> ORGANISM: vaccinia virus

<400> SEQUENCE: 2

Met Leu Ala Phe Cys Tyr Ser Leu Pro Asn Ala Gly Asp Val Ile Lys
1               5                   10                  15

Gly Arg Val Tyr Glu Lys Asp Tyr Ala Leu Tyr Ile Tyr Leu Phe Asp
                20                  25                  30

Tyr Pro His Phe Glu Ala Ile Leu Ala Glu Ser Val Lys Met His Met
            35                  40                  45

Asp Arg Tyr Val Glu Tyr Arg Asp Lys Leu Val Gly Lys Thr Val Lys
 50                  55                  60

Val Lys Val Ile Arg Val Asp Tyr Thr Lys Gly Tyr Ile Asp Val Asn
65                  70                  75                  80

Tyr Lys Arg Met Cys Arg His Gln
                85

<210> SEQ ID NO 3
<211> LENGTH: 88
<212> TYPE: PRT
<213> ORGANISM: teterapox virus

<400> SEQUENCE: 3

Met Leu Ala Phe Cys Tyr Ser Leu Pro Asn Val Gly Asp Val Leu Lys
1               5                   10                  15

Gly Lys Val Tyr Glu Asn Gly Tyr Ala Leu Tyr Ile Asp Leu Phe Asp
                20                  25                  30

Tyr Pro His Ser Glu Ala Ile Leu Ala Glu Ser Val Gln Met His Met
            35                  40                  45

Asn Arg Tyr Phe Lys Tyr Arg Asp Lys Leu Val Gly Lys Thr Val Lys
 50                  55                  60

Val Lys Val Ile Arg Val Asp Tyr Thr Lys Gly Tyr Ile Asp Val Asn
65                  70                  75                  80

Tyr Lys Arg Met Cys Arg His Gln
                85

<210> SEQ ID NO 4
<211> LENGTH: 89
<212> TYPE: PRT
<213> ORGANISM: sheeppox virus

<400> SEQUENCE: 4

Met Ser Ser Asn Ser Asp Leu Ala Phe Cys Tyr Val Leu Pro Asn Ile
1               5                   10                  15

Asn Glu Val Thr Asp Gly Ile Val Cys Ile Arg Asp Asn Ile Val Tyr
                20                  25                  30

Val Lys Leu Ile Asn Tyr Gly Leu Glu Ala Leu Val Ile Asp Tyr Val

```
                35                  40                  45
Asn Ile Asn Met Asp Gln Met Asn Asn Ile Lys Lys Thr Leu Val Asn
         50                  55                  60
Lys Leu Ile Asn Val Gln Ile Ile Arg Met Asn Lys Ile Lys Gly Tyr
 65                  70                  75                  80
Ile Asp Val Lys Ile Tyr Asn Asn Asn
                 85

<210> SEQ ID NO 5
<211> LENGTH: 88
<212> TYPE: PRT
<213> ORGANISM: Yaba monkey tumor virus

<400> SEQUENCE: 5

Met Ser Arg Asn Arg Ser Gln Leu Ala Phe Cys Tyr Ala Phe Pro Thr
 1               5                  10                  15
Val Gly Thr Ile Thr Lys Gly Val Val Thr Val Glu Gly Asp Ser Phe
                20                  25                  30
Thr Val Phe Leu Pro Glu Phe Gly Leu His Ala Leu Ile Val Asn Tyr
            35                  40                  45
Leu Ser Val Asn Val Lys Arg Ala Lys Lys Leu Ser Glu Lys Leu Ser
         50                  55                  60
Gly Lys Thr Val Thr Val Gln Val Ile Arg Thr Asp Lys Leu Lys Gly
 65                  70                  75                  80
Tyr Val Asp Val Arg His Ile Glu
                 85

<210> SEQ ID NO 6
<211> LENGTH: 86
<212> TYPE: PRT
<213> ORGANISM: suipoxvirus

<400> SEQUENCE: 6

Met Ser Thr Met Asn Thr Leu Ala Phe Cys Tyr Gly Leu Pro Asn Ile
 1               5                  10                  15
Asn Asp Ile Thr Gln Gly Ile Ile Phe Val Arg Asn Asn Ile Phe Tyr
                20                  25                  30
Ser Tyr Leu Thr Asp Tyr Ala Met Glu Ala Cys Ile Leu Asn Tyr Ile
            35                  40                  45
Asn Ile Arg Ala Asp Lys Ile Glu Asp Leu Lys Lys Ser Leu Val Gly
         50                  55                  60
Lys Thr Ile Ser Val Arg Val Ile Arg Val Asp Val Leu Lys Gly Tyr
 65                  70                  75                  80
Ile Asp Val Ser Ile Val
                 85

<210> SEQ ID NO 7
<211> LENGTH: 102
<212> TYPE: PRT
<213> ORGANISM: myxomavirus

<400> SEQUENCE: 7

Met Thr Val Ile Lys Pro Ser Ser Arg Pro Arg Pro Arg Lys Asn Lys
 1               5                  10                  15
Asn Ile Lys Val Asn Thr Tyr Arg Thr Ser Ala Met Asp Leu Ser Pro
                20                  25                  30
Gly Ser Val His Glu Gly Ile Val Tyr Phe Lys Asp Gly Ile Phe Lys
            35                  40                  45
```

```
Val Arg Leu Gly Tyr Glu Gly His Glu Cys Ile Leu Leu Asp Tyr
        50                  55                  60

Leu Asn Tyr Arg Gln Asp Thr Leu Asp Arg Leu Lys Glu Arg Leu Val
 65                  70                  75                  80

Gly Arg Val Ile Lys Thr Arg Val Val Arg Ala Asp Gly Leu Tyr Val
                 85                  90                  95

Asp Leu Arg Arg Phe Phe
            100
```

<210> SEQ ID NO 8
<211> LENGTH: 88
<212> TYPE: PRT
<213> ORGANISM: artificial
<220> FEATURE:
<223> OTHER INFORMATION: synthetic vaccinia virus K3 mutant K45E

<400> SEQUENCE: 8

```
Met Leu Ala Phe Cys Tyr Ser Leu Pro Asn Ala Gly Asp Val Ile Lys
 1               5                  10                  15

Gly Arg Val Tyr Glu Lys Asp Tyr Ala Leu Tyr Ile Tyr Leu Phe Asp
                 20                  25                  30

Tyr Pro His Phe Glu Ala Ile Leu Ala Glu Ser Val Glu Met His Met
             35                  40                  45

Asp Arg Tyr Val Glu Tyr Arg Asp Lys Leu Val Gly Lys Thr Val Lys
         50                  55                  60

Val Lys Val Ile Arg Val Asp Tyr Thr Lys Gly Tyr Ile Asp Val Asn
 65                  70                  75                  80

Tyr Lys Arg Met Cys Arg His Gln
                 85
```

<210> SEQ ID NO 9
<211> LENGTH: 88
<212> TYPE: PRT
<213> ORGANISM: artificial
<220> FEATURE:
<223> OTHER INFORMATION: vaccinia virus K3 mutant K45T

<400> SEQUENCE: 9

```
Met Leu Ala Phe Cys Tyr Ser Leu Pro Asn Ala Gly Asp Val Ile Lys
 1               5                  10                  15

Gly Arg Val Tyr Glu Lys Asp Tyr Ala Leu Tyr Ile Tyr Leu Phe Asp
                 20                  25                  30

Tyr Pro His Phe Glu Ala Ile Leu Ala Glu Ser Val Thr Met His Met
             35                  40                  45

Asp Arg Tyr Val Glu Tyr Arg Asp Lys Leu Val Gly Lys Thr Val Lys
         50                  55                  60

Val Lys Val Ile Arg Val Asp Tyr Thr Lys Gly Tyr Ile Asp Val Asn
 65                  70                  75                  80

Tyr Lys Arg Met Cys Arg His Gln
                 85
```

<210> SEQ ID NO 10
<211> LENGTH: 88
<212> TYPE: PRT
<213> ORGANISM: artificial
<220> FEATURE:
<223> OTHER INFORMATION: synthetic vaccinia virus K3 mutant E53K

<400> SEQUENCE: 10

```
Met Leu Ala Phe Cys Tyr Ser Leu Pro Asn Ala Gly Asp Val Ile Lys
1               5                   10                  15

Gly Arg Val Tyr Glu Lys Asp Tyr Ala Leu Tyr Ile Tyr Leu Phe Asp
            20                  25                  30

Tyr Pro His Phe Glu Ala Ile Leu Ala Glu Ser Val Lys Met His Met
        35                  40                  45

Asp Arg Tyr Val Lys Tyr Arg Asp Lys Leu Val Gly Lys Thr Val Lys
    50                  55                  60

Val Lys Val Ile Arg Val Asp Tyr Thr Lys Gly Tyr Ile Asp Val Asn
65                  70                  75                  80

Tyr Lys Arg Met Cys Arg His Gln
                85
```

```
<210> SEQ ID NO 11
<211> LENGTH: 89
<212> TYPE: PRT
<213> ORGANISM: artificial
<220> FEATURE:
<223> OTHER INFORMATION: synthetic sheeppox virus K3 ortholog mutant
      Y47H

<400> SEQUENCE: 11

Met Ser Ser Asn Ser Asp Leu Ala Phe Cys Tyr Val Leu Pro Asn Ile
1               5                   10                  15

Asn Glu Val Thr Asp Gly Ile Val Cys Ile Arg Asp Asn Ile Val Tyr
            20                  25                  30

Val Lys Leu Ile Asn Tyr Gly Leu Glu Ala Leu Val Ile Asp His Val
        35                  40                  45

Asn Ile Asn Met Asp Gln Met Asn Asn Ile Lys Lys Thr Leu Val Asn
    50                  55                  60

Lys Leu Ile Asn Val Gln Ile Ile Arg Met Asn Lys Ile Lys Gly Tyr
65                  70                  75                  80

Ile Asp Val Lys Ile Tyr Asn Asn Asn
                85
```

```
<210> SEQ ID NO 12
<211> LENGTH: 9
<212> TYPE: PRT
<213> ORGANISM: artificial
<220> FEATURE:
<223> OTHER INFORMATION: C domain consensus sequence from vaccinia and
      teterapox virus
<220> FEATURE:
<221> NAME/KEY: VARIANT
<222> LOCATION: (1)..(1)
<223> OTHER INFORMATION: K or Q
<220> FEATURE:
<221> NAME/KEY: VARIANT
<222> LOCATION: (5)..(5)
<223> OTHER INFORMATION: D or N
<220> FEATURE:
<221> NAME/KEY: VARIANT
<222> LOCATION: (8)..(8)
<223> OTHER INFORMATION: v or f
<220> FEATURE:
<221> NAME/KEY: VARIANT
<222> LOCATION: (9)..(9)
<223> OTHER INFORMATION: E or K

<400> SEQUENCE: 12

Xaa Met His Met Xaa Arg Tyr Xaa Xaa
1               5
```

```
<210> SEQ ID NO 13
```

```
<211> LENGTH: 88
<212> TYPE: PRT
<213> ORGANISM: artificial
<220> FEATURE:
<223> OTHER INFORMATION: consensus sequence for K3 of vaccinia and
      teterapox viruses
<220> FEATURE:
<221> NAME/KEY: variant
<222> LOCATION: (11)..(11)
<223> OTHER INFORMATION: a or v
<220> FEATURE:
<221> NAME/KEY: variant
<222> LOCATION: (15)..(15)
<223> OTHER INFORMATION: i or l
<220> FEATURE:
<221> NAME/KEY: variant
<222> LOCATION: (18)..(18)
<223> OTHER INFORMATION: i or l
<220> FEATURE:
<221> NAME/KEY: variant
<222> LOCATION: (22)..(22)
<223> OTHER INFORMATION: k or n
<220> FEATURE:
<221> NAME/KEY: variant
<222> LOCATION: (23)..(23)
<223> OTHER INFORMATION: d or g
<220> FEATURE:
<221> NAME/KEY: variant
<222> LOCATION: (29)..(29)
<223> OTHER INFORMATION: y or d
<220> FEATURE:
<221> NAME/KEY: variant
<222> LOCATION: (36)..(36)
<223> OTHER INFORMATION: f or s
<220> FEATURE:
<221> NAME/KEY: variant
<222> LOCATION: (45)..(45)
<223> OTHER INFORMATION: k or q
<220> FEATURE:
<221> NAME/KEY: variant
<222> LOCATION: (49)..(49)
<223> OTHER INFORMATION: d or n
<220> FEATURE:
<221> NAME/KEY: variant
<222> LOCATION: (52)..(52)
<223> OTHER INFORMATION: v or f
<220> FEATURE:
<221> NAME/KEY: variant
<222> LOCATION: (53)..(53)
<223> OTHER INFORMATION: e or k

<400> SEQUENCE: 13

Met Leu Ala Phe Cys Tyr Ser Leu Pro Asn Xaa Gly Asp Val Xaa Lys
1               5                   10                  15

Gly Xaa Val Tyr Glu Xaa Xaa Tyr Ala Leu Tyr Ile Xaa Leu Phe Asp
            20                  25                  30

Tyr Pro His Xaa Glu Ala Ile Leu Ala Glu Ser Val Xaa Met His Met
        35                  40                  45

Xaa Arg Tyr Xaa Xaa Tyr Arg Asp Lys Leu Val Gly Lys Thr Val Lys
    50                  55                  60

Val Lys Val Ile Arg Val Asp Tyr Thr Lys Gly Tyr Ile Asp Val Asn
65                  70                  75                  80

Tyr Lys Arg Met Cys Arg His Gln
                85
```